(12) United States Patent
Zhou

(10) Patent No.: US 8,969,422 B2
(45) Date of Patent: Mar. 3, 2015

(54) METHOD, SYSTEM AND EQUIPMENT FOR GASIFICATION-LIQUEFACTION DISPOSAL OF MUNICIPAL SOLID WASTE

(75) Inventor: Kaigen Zhou, Quzhou (CN)

(73) Assignee: Quzhou City Guangyuan Domestic Garbage Liquefy Technology Institute, Quzhou (CN)

( * ) Notice: Subject to any disclaimer, the term of this patent is extended or adjusted under 35 U.S.C. 154(b) by 349 days.

(21) Appl. No.: 13/634,787

(22) PCT Filed: Mar. 7, 2011

(86) PCT No.: PCT/CN2011/000363
§ 371 (c)(1),
(2), (4) Date: Sep. 13, 2012

(87) PCT Pub. No.: WO2011/113298
PCT Pub. Date: Sep. 22, 2011

(65) Prior Publication Data
US 2013/0012605 A1 Jan. 10, 2013

(30) Foreign Application Priority Data

Mar. 13, 2010 (CN) .................. 2010 2 0160039 U
Apr. 28, 2010 (CN) .................... 2010 1 0173404

(51) Int. Cl.
*C07C 27/00* (2006.01)
*C01B 3/24* (2006.01)
(Continued)

(52) U.S. Cl.
CPC ......... *C05F 17/0027* (2013.01); *C07C 29/1518* (2013.01); *B09B 3/0083* (2013.01);
(Continued)

(58) Field of Classification Search
USPC .......... 518/700; 48/127.1, 127.9, 128, 197 R, 48/198.3; 422/148, 187
See application file for complete search history.

(56) References Cited

U.S. PATENT DOCUMENTS

2007/0289509 A1 12/2007 Vera

FOREIGN PATENT DOCUMENTS

CN 101440971 A 5/2009
CN 101468788 A 7/2009
(Continued)

*Primary Examiner* — Jafar Parsa
(74) *Attorney, Agent, or Firm* — Jacobson Holman PLLC; Jiwen Chen

(57) ABSTRACT

A gasification-liquefaction disposal method, system and equipment for MSW are disclosed. The method involves the MSW pretreatment of dehydrating and separating, thus reducing water and inorganic substance content of the waste. Then, the MSW is introduced into a plasma gasifier (23) by a carbon dioxide air-sealed feeding device (13) and gasified therein to obtain hydrogen-rich syngas. The hydrogen-rich syngas is then cooled, deacidified, dedusted and separated to obtain carbon dioxide. Then, the hydrogen-rich syngas is catalyzed to produce methanol product in a methanol synthesis reactor (52). The separated carbon dioxide is sent back to a carbonation reaction chamber (2007) of a gasification system to perform carbonation reaction with calcium oxide, thereby releasing heat to provide assistant heat energy for gasification and avoiding greenhouse gas from being discharged into environment. Exhaust gas is returned to the plasma gasifier (23) for remelting treatment, thus forming a closed-loop circulation production system and realizing the disposal of the MSW with zero discharge and no pollution, thereby avoiding dioxin pollution and converting the MSW to chemical raw materials and fuel needed by mankind. The method, system and equipment are suitable for harmless and recycling disposal of MSW, industrial high polymer waste, composting waste and waste in waste sorting sites.

10 Claims, 10 Drawing Sheets

(51) Int. Cl.

| | | |
|---|---|---|
| B01J 8/00 | (2006.01) | |
| C01C 1/00 | (2006.01) | |
| B01J 10/00 | (2006.01) | |
| C05F 17/00 | (2006.01) | |
| C07C 29/151 | (2006.01) | |
| B09B 3/00 | (2006.01) | |
| C10J 3/18 | (2006.01) | |
| C10J 3/30 | (2006.01) | |
| C10K 1/00 | (2006.01) | |
| C10K 1/02 | (2006.01) | |
| C10K 1/12 | (2006.01) | |
| C10K 1/20 | (2006.01) | |
| C05F 9/00 | (2006.01) | |

(52) U.S. Cl.
CPC ... *C10J 3/18* (2013.01); *C10J 3/30* (2013.01); *C10K 1/005* (2013.01); *C10K 1/024* (2013.01); *C10K 1/026* (2013.01); *C10K 1/122* (2013.01); *C10K 1/20* (2013.01); *C05F 9/00* (2013.01); *C10J 2300/0946* (2013.01); *C10J 2300/0906* (2013.01); *C10J 2300/0996* (2013.01); *C10J 2300/1238* (2013.01); *C10J 2300/1634* (2013.01); *C10J 2300/1665* (2013.01); *C10J 2300/1668* (2013.01); *C10J 2300/1807* (2013.01); *Y02E 50/32* (2013.01)
USPC ......... 518/700; 518/702; 48/127.1; 48/127.9; 48/128; 48/197 R; 48/198.3; 422/148; 422/187

(56) References Cited

FOREIGN PATENT DOCUMENTS

| | | |
|---|---|---|
| CN | 101565629 A | 10/2009 |
| WO | WO2004041974 A1 | 5/2004 |
| WO | WO2004044492 A1 | 5/2004 |
| WO | WO200844216 A1 | 4/2008 |
| WO | WO2010019662 A1 | 2/2010 |

METHOD, SYSTEM AND EQUIPMENT FOR GASIFICATION-LIQUEFACTION DISPOSAL OF MUNICIPAL SOLID WASTE

This is a U.S. national stage application of PCT Application No. PCT/CN2011/000363 under 35 U.S.C. 371, filed Mar. 7, 2011 in Chinese, claiming the priority benefit of Chinese Application No. 201020160039.7, filed Mar. 13, 2010, and Chinese Application No. 201010173404.2, filed Apr. 28, 2010, both of which are hereby incorporated by reference.

FIELD OF THE INVENTION

The present invention relates to the technology of solid waste disposal, and more specially relates to a method and equipment for the disposal of municipal solid waste (hereinafter referred to as MSW) or organic waste.

DESCRIPTION OF THE PRIOR ART

With growing economic development and constant expansion of city scale, municipal solid waste and organic waste are rapidly increasing like a flood. Now garbage besiege appear in many cities of many countries, affecting sustainable economic development and restricting urban development. MSW and organic waste contain many harmful ingredients that, if not handled properly, will pollute environment and threaten human health. Presently, MSW disposal technology mainly includes garbage sorting and comprehensive utilization, sanitary landfill, composting (biochemical) and incineration. Among these technologies, garbage sorting has not been implemented in many countries because it requires public participation. Even if garbage is sorted and comprehensively utilized, there is still an amount of 40-50% of waste requiring incineration or landfill. In most parts of the world, sanitary landfill is adopted to dispose urban MSW, which occupies a lot of land resource, releases a lot of greenhouse gas, pollutes land and groundwater and destroys living environment of mankind Composting technology only makes use of about 40% organic substances, and the rest 60% still needs the disposal of incineration or landfill which also meets the problem of secondary pollution. Incineration of MSW seemingly reduces the amount and resource of garbage. However, in fact, this method transfers solid pollutant to the atmosphere in the form of flue gas that will return to the earth by cross-ventilation and gravitational force or in the form of acid rain, affecting human health and environment with the carbon dioxide emissions from the greenhouse effect. Incineration also easily generates dioxin—highly carcinogenic toxic substance—to pollute environment and harm human health. Even with flue gas purification system, waste incineration still lacks effective and reliable end purification technology to eliminate dioxin pollution.

Dioxin is a chlorine-containing strongly toxic organic chemical. It is a very stable, water-insoluble, colorless and odorless liposoluble material, and it easily bioaccumulates. Since the microorganisms and the hydrolysis in natural world hardly impact the molecular structure of dioxin, dioxin in the environment is difficult to eliminate by natural degradation. Dioxin known as the "poison of the century" has been claimed to be as a category one carcinogen by the international cancer research centers. Garbage, industrial organic waste and medical waste will produce dioxin in the incineration process in the following ways: a. the formation of dioxin in the burning process by molecular rearrangement, free-radical condensation, dechlorination or other molecule reaction of chlorine-containing precursors such as chlorinated plastics, chlorinated pesticides/herbicide/wood preservative/bleach/food, and polychlorinated biphenyl; b. when the combustion is not sufficient, chlorine-containing garbage will not be completely burned, resulting in excessive unburned substances in the flue gas that will form dioxin when meeting strong catalytic substances such as copper chloride, iron chloride, nickel oxide, aluminum oxide and other heavy metals; c. dioxin contained in the fuel is not destroyed and still exists in the flue gas after burning; d. residual carbon, oxygen, hydrogen, chloride, etc. in solid fly ash are catalyzed in the surface of fly ash and synthesize intermediate material or dioxin, or precursors in vapor phase are catalyzed in the surface of fly ash and synthetize dioxin; e. when the flue gas drops from the high temperature to low temperature between 250° C. to 500° C., the decomposed dioxin will be resynthesized; f. dioxin is composed by unknown reasons. MSW commonly contains chlorine source, organic matter and heavy metals. Therefore, the flue gas, fly ash and slag out of incinerator often contain dioxin. Studies have shown that the precursor concentration, chlorine concentration, temperature, oxygen content, sulfur content, and heavy metals as the existence of unconscious catalysts produce significant impact on the generation and emission of dioxin in the process of MSW incineration. Even with the most advanced incineration technology and equipment, waste incineration inevitably produces dioxin-contaminated environment. Therefore, complete combustion of garbage can only be under the conditions of >6% excessive oxygen, otherwise more pollution will be produced. Excessive oxygen is one of the conditions to form dioxin. The dioxin concentration is greatly increased in the environment of excessive oxygen while it is decreased in oxygen-deficient environment. No oxygen, no dioxin can be synthesized. The flue gas must contact the metal heating surfaces of the superheater, boiler, heat exchangers, and air preheater equipment during incineration. So all the metal heating surfaces will become the catalytic media of dioxin. Complete deacidification is difficult to realize during incineration. The residual carbon, oxygen, hydrogen, chlorine, fly ash and a certain amount of dioxin precursors still exist in the flue gas, and will inevitably resynthesize dioxin at a lower temperature outside the incinerator. There is a certain amount of dioxin in the flue gas of garbage incinerator. It is difficult to eliminate dioxin from the flue gas. It will pollute the environment with the flue gas emissions. Since it is hard to degrade and has a half-life of 273 years, dioxin is basically considered nondegradable. It will be accumulated more and more in people's living environment and in human body. Serious dioxin pollution appears in many countries that mainly adopt garbage incineration, to which sufficient attention should be paid.

In summary, the disposal of garbage incineration is not a good way. Sanitary landfill occupies land, releases greenhouse gases and pollutes environment. Waste sorting and composting have to face the problem that a part of garbage cannot be fully used. However, the headache garbage besiege must be solved. Therefore, humanity is eager to get perfect technical solutions for the garbage disposal.

SUMMARY OF THE INVENTION

The object of the present invention is to overcome the problems of garbage landfill and incineration that harm human living environment with dioxin contamination by disclosing a technology to dispose MSW and organic waste by gasification-liquefaction technology that effectively inhibit the formation of pollutants including dioxin. No greenhouse gas emits throughout the process of disposal. Therefore, the technology can solve the problem of dioxin contamination, protect ecological environment, and convert the garbage, organic waste to a chemical raw material or clean energy.

One method of the present invention to dispose MSW by gasification—gasification technology, comprising calcium oxide assisting plasma gasification technology wherein the MSW or organic waste, after pretreatment, is dehydrated and separated, thus reducing the moisture and mineral content, decreasing the unnecessary components in raw material in the furnace, increasing calorific value, lowering electric consumption of plasma gasification furnace and improving the quality of syngas. After pretreatment, MSW or organic waste is fed into a plasma gasifier via a $CO_2$ sealed feeding device. $CO_2$ seal can effectively prevent air from entering through feeding inlet into the gasifier as well as prevent the syngas in the furnace from escaping through the feeding inlet, but not obstruct feeding material. A plasma gasifier is provided with a drying section, a pyrolysis section and a gasification section in the order of upper, middle and lower segments. The MSW or organic waste, after dried and pyrolyze in the furnace, becomes waste carbon, and is fed in gasification zone for gasification reaction with the decomposer of the water steam injected into the gasification zone from a plasma torch, and generates hydrogen-rich syngas in which CO and $H_2$ are the main components. A plasma torch is provided in the gasification section and uses water steam as gasifying agent and working gas. The water steam is heated by the plasma torch to >4200° C., so that water molecules are decomposed completely, generating $H^*$, $H_2^*$, $HO^*$, $O^*$, $O_2^*$ and $H_2O^*$ that are then directly sprayed on the MSW carbon in the gasification section. The MSW carbon serves as hydrogen and oxygen absorber to generate CO and $H_2$. The clinker is melted to a liquid slag at 1300~1600° C. environment in melted slag zone of the furnace, and discharged via a water seal to a slag pool. The calcium oxide assisting plasma gasification is adopted. A carbonator reaction chamber is provided in the gasification system. The heat emitted by carbon dioxide absorbing calcium oxide to generate calcium carbonate can provide supplementary heat source for the gasification, drying and preheating of new waste materials fed in the furnace, so as to reduce the energy consumption of the plasma torch. The pyrolysis gas produced at the pyrolysis section of a plasma gasifier is introduced into a carbonator reaction chamber, and then as a carrier gas, the pyrolysis gas carries calcium oxide, calcium carbonate mixture and heat into the drying section of the plasma gasifier. Also serving as a dechlorination or desulfurizing agent, calcium oxide can remove dioxin precursors, chlorides and sulfides in the environment of excessive calcium oxide. Then the pyrolysis gas is introduced into a gas-solid separator wherein calcium oxide and calcium carbonate are separated, and then fed into the gasification section of the plasma gasifier. In the environment of 1000 to 1300° C., methane, gaseous tar, ethylene, ethane, water steam, etc., are pyrolyzed and chemically reacted, thoroughly decomposing dioxin at the same time. By circulated gasification, the waste in the furnace is completely decomposed, and produces a hydrogen-rich syngas wherein high-quality hydrogen and carbon monoxide are main components. The hydrogen-rich syngas is outputted out of the plasma gasifier, and after cooling in an exhaust heat boiler, deacidified and dedusted in gas purifying equipment that consists of an absorption reactor, a cyclone duster and a bag dust collector. Then carbon dioxide in the syngas is absorbed by potassium carbonate solution in $CO_2$ absorbing tower to generate potassium bicarbonate. The syngas after removing carbon dioxide is fed in a methanol synthesis reactor to produce methanol and the potassium bicarbonate is fed to the regeneration reactor to decompose to potassium carbonate solution and carbon dioxide by heating. The decomposed potassium carbonate solution is then returned to the $CO_2$ absorbing tower for recycling and the decomposed carbon dioxide is fed into the carbonation reaction chamber of the gasification system for carbonation reaction with calcium oxide, thus assisting heat to waste gasification while preventing greenhouse gases from emitting. Hydrogen-rich syngas is catalyzed to a methanol product in the methanol synthesis reactor. The methanol product is mixed with limewater in a mixed absorber of end purifying device to allow the residual contaminants including dioxin, carbon dioxide to be absorbed by the limewater. Then the methanol is separated out through a distillation column, and unreacted gas is returned to the methanol synthesis reactor for a circulating reaction. After decontamination, limewater is fed by a circulating pump back to the mixed absorber for recycling. The exhaust is returned to the plasma gasifier for recycling, forming a closed loop production system. In this method, the operating temperature of drying section is controlled at between 120 to 300° C.; the operating temperature of pyrolysis section is controlled between 300 to 1000° C.; the operating temperature of gasification zone is controlled at between 1000 to 1300° C.; the operating pressure in the gasifying furnace is controlled at between −30 Pa~+5 kPa. When clinker is melted to liquid slag and discharged, a liquid slag zone is provided between gasification zone and slag port, and a plasma torch is provided in the slag zone. The operating temperature of the slag zone is controlled at between 1300~1600° C. The leachate generated in waste pretreatment process is fed into a digester for biogas production by anaerobic fermentation. The biogas is then fed into the plasma gasifier for decomposition, and biogas residue can be used as fertilizer. Selected inorganic materials sorted in the pretreatment process are resorted for scrap metal recycling. Then non-metallic inorganic materials are ground and mixed with calcium carbonate, calcium oxide separated from the gasification system to produce non-fired bricks. The slag discharged from plasma gasifier into water sealed slag pool becomes vitreous particles that can be directly used as building material. The fly ash collected from the bag filter is then treated through melting kiln and the slag can be directly used as building material.

According to the above method, the amount of calcium oxide that is input to carbonation reaction chamber is determined by 1.2~1.5 times the total amount of molar number of carbon dioxide, chloride, sulfide, and fluoride in the reaction chamber. The molar number of carbon dioxide is determined by real input amount and detected content in pyrolysis gas. The molar number of chloride, sulfide, and fluoride is determined by the analysis of organic waste in sampled waste.

In the above-mentioned method, the waste is disposed by the way of plasma gasification such as water steam, without inputting oxygen or air to the gasifier, so that waste is gasified in anoxic environments. The rate of excessive oxide in syngas is none that can effectively inhibit the production of dioxin. In the carbonation reaction chamber, directly mixing calcium oxide powder with the pyrolysis gas can effectively remove the precursors of dioxin, chlorinated organics, desulfurize and cure in the absorbent, thereby reducing the probability of dioxin formation. The pyrolysis gas is circulated in the plasma gasifier. When the pyrolysis gas is circulated to the gasification section at 1000~1300° C., dioxin will be thoroughly destroyed. In the plasma gasifier, waste materials are first pyrolyzed, after volatile constituents are escaped, go through gasification reaction with a plasma active material of the water steam at over 4200° C. and fixed carbon. In the gasification zone at 1000~1600° C., the fixed carbon will be completely gasified. Using a closed loop production process, MSW and organic waste are absorbed with limewater in terminal purification operation and converted into methanol products for human needs.

A MSW gasification-liquefaction disposal system of the present invention including a plasma gasification equipment, comprises a preprocessing device, a $CO_2$ gas sealed feeding means (13), a plasma gasifier (23), a plasma torch (24), a gas-solid separator (17), a circulating fan (18), a heat exchanger a (20), a carbonation reaction chamber (2007), a waste heat boiler (27), an absorption reactor (32), a cyclone duster (31), a bag dust collector (38), $CO_2$ absorber (42), a regeneration tower (46), a methanol synthesis reactor (52), a mixed absorber (55), a distillation column (62), a decontaminator (58), a circulating pump (60), a methanol tank (65) and connecting ducts. Among them: the preprocessing device comprises a waste storage pit (2) and a sorting machine (3). The inner space of plasma gasifier (23) is provided with a drying section, a pyrolysis section and a gasification section. In the drying section are provided waste material inlet, heat carried gas inlet and pyrolysis gas outlet. The output interface of heat carried gas is provided in the pyrolysis section. The input interface of pyrolysis gas is provided in the gasification section. The output interface of syngas is provided in the joint position of pyrolysis section and the gasification section. The plasma torch (24) is provided in the gasification zone in the lower part of the plasma gasifier (23). The heat exchanger a (20) consists of an atmolysis chamber, a heat exchange chamber and a gas collection chamber. The input interface of pyrolysis gas is provided in the atmolysis chamber. The output interface of heat carried gas is provided in the heat change chamber. The output interface of pyrolysis gas is provided in the gas collection chamber. The carbonation reaction chamber (2007) communicates directly with the heat exchange chamber in the heat exchanger a (20). The carbonation reaction chamber (2007) is provided with the input interface of heat carried gas, inputting apparatus of the calcium oxide and input interface of carbon dioxide. A $CO_2$ absorber (42) is provided with the input interface of the syngas, the output interface of syngas, $KHCO_3$ output interface and the input interface of the $K_2CO_3$ solution. A regeneration tower (46) is provided with the input interface of $KHCO_3$, the output interface of $CO_2$ and the output interface of the $K_2CO_3$ solution.

A waste storage pit (2) is constantly connected with a sorting machine (3) through a crane grab (1). The sorting machine (3) is constantly connected with a feed inlet of the $CO_2$ gas sealed feeding means (13) of plasma gasification equipment by the belt conveyor or screw feeders. The outlet of $CO_2$ gas sealed feeding means (13) is connected to the waste inlet of the plasma gasifier (23). The output interface of heat carried gas of the plasma gasifier (23) is connected to the input interface of heat carried gas of carbonation reaction chamber (2007). The output interface of heat carried gas of the heat exchanger (20) is connected to the inlet heat carried gas of the plasma gasifier (23). The outlet of heat carried gas of the plasma gasifier (23) is connected to the mixture inlet of the gas-solid separator (17). The gaseous substance outlet of the gas-solid separator (17) is connected to the input interfaces of pyrolysis gas of the heat exchanger a (20) through the circulating fan (18). The output interface of pyrolysis gas of the heat exchanger a (20) is connected to the input interface of pyrolysis gas of the plasma gasifier (23). The output interface of syngas of the plasma gasifier (23) is connected to the input interface of syngas of the waste heat boiler (27). The output interface of syngas of the waste heat boiler (27) is connected to the input interface of syngas of an absorption reactor (32).

The output interface of syngas of the absorption reactor (32) is connected to the mixture input interface of syngas of a cyclone duster (31). The solid substance outlet of the cyclone duster (31) is connected to the connecting pipe of syngas input interface of a absorption reactor (32). The solid gaseous substance outlet of the cyclone duster (31) is connected to the syngas input interface of a bag dust collector (38). The output interface of syngas of the bag dust collector (38) is connected to syngas input interface of a $CO_2$ absorbing tower (42). The output interface of $KHCO_3$ of the $CO_2$ absorbing tower (42) is connected to an input interface of $KHCO_3$ of a regeneration tower (46). The $CO_2$ output interface of the regeneration tower (46) is connected to the input interface of $CO_2$ of a carbonation reaction chamber (2007). The output interface of $K_2CO_3$ solution of a regenerating tower (46) is connected to the input interface of $K_2CO_3$ solution of the $CO_2$ absorbing tower (42). The output interface of syngas of the $CO_2$ absorbing tower (42) is connected to the induction port of compressor i (51). The exhaust port of the compressor i (51) is connected to the virgin gas port of a methanol synthesis reactor (52). The methanol gas outlet of the methanol synthesis reactor (52) is connected to methanol gas inlet of the mixed absorber (55). The mixture outlet of mixed absorber (55) is connected to the mixture input interface of a distillation column (62). The unreacted gas outlet of distillation column (62) of is connected to the return-air interface of the methanol synthesis reactor (52) via an unreacted gas pipeline (61) and compressor b (56). The methanol product outlet of the distillation column (62) is connected to a methanol tank (65). The limewater outlet of distillation column (62) is connected to the input interface of decontaminator (58). The limewater outlet of decontaminator (58) is connected to the water inlet of a circulating pump (60). The water outlet of the circulation pump (60) is connected to the limewater inlet of a mixed absorber (55).

In the system described above, the preprocessing device further comprises a spiral moisture expelling and feeding means (10) and a digester (9). The spiral moisture expelling and feeding means (10) performs dual functions of water squeeze and material feeding. The spiral moisture expelling and feeding means (10) is provided between the sorting machine (3) and $CO_2$ gas sealed feeding means (13). The waste material outlet of the sorting machine (3) is constantly connected to the hopper of spiral moisture expelling and feeding means (10) through a belt conveyor (8). The material outlet of spiral moisture expelling and feeding means (10) is connected to the material inlet of $CO_2$ gas sealed feeding means (13) through a duct a (12). The outlet of $CO_2$ gas sealed feeding means (13) is connected to the material inlet of the plasma gasifier (23) through a duct b (14). The leachate interfaces of the waste storage pit (2), the sorting machine (3) and spiral moisture expelling and feeding means (10) are connected to the material outlet of the digester (9). The biogas outlet of the digester (9) is connected to the gasification zone of the plasma gasification furnace (23).

In the above-described system, an induced-draft fan (40) and a carbon monoxide conversion reactor (41) are also provided between a bag dust collector (38) and a $CO_2$ absorber (42). The output interface of syngas of the bag dust collector (38) is connected to the suction inlet of a induced-draft fan (40). The air outlet of induced-draft fan (40) is connected to the syngas input interface of a CO shift reactor (41). The output interface of syngas of the CO shift reactor (41) is connected to syngas input interface of $CO_2$ absorbing tower (42). A compressor a (44) and a syngas storage tank (48) are also provided between the $CO_2$ absorbing tower (42) and a compressor i (51). The output interface of syngas of the $CO_2$ absorbing tower (42) is connected to the induction port of the compressor a (44). The exhaust port of the compressor a (44) is connected to the input interface of a syngas storage tank (48). The output interface of syngas storage tank (48) is connected to the suction port of the compressor i (51).

In the system described above, an exhaust gas interface and the ammonia plant are provided in an unreacted gas pipeline (61) at the terminal end of the methanol synthesis system, and meanwhile an exhaust feedback pipeline (30) is provided between the plasma gasifier (23) and purification equipment at the terminal end. The exhaust gas interface of the unreacted gas pipeline (61) is, via a control valve, respectively connected to the exhaust feedback pipeline (30) of the plasma gasifier (23) and material inlet interface of synthetic ammonia equipment. The exhaust gas outlet of synthetic ammonia equipment is connected to the exhaust feedback pipeline (30) of the plasma gasifier (23).

Another MSW gasification-liquefaction disposal system of the present invention including a plasma gasification equipment, comprises a preprocessing device, a $CO_2$ gas sealed feeding means (13), a plasma gasifier (23), a plasma torch (24), a circulating fan (18), a heat exchanger b (21), a waste heat boiler (27), an absorption reactor (32), a cyclone duster (31), a bag dust collector (38), a hydrogenation absorber (49), a methanol synthesis reactor (52), a mixed absorber (55), a distillation column (62), a decontaminator (58), a circulating pump (60), a methanol tank (65) and connecting ducts. Among them: the preprocessing device comprises a waste storage pit (2) and a sorting machine (3). The inner space of plasma gasifier (23) is provided with drying section, pyrolysis section and gasification section. In the drying section are provided waste material inlet and pyrolysis gas outlet. The input interface of pyrolysis gas is provided in the gasification section. The output interface of syngas is provided in the joint position of pyrolysis section and the gasification section. The plasma torch (24) is provided in gasification section in the lower part of the plasma gasifier (23). Heat exchanger b (21) consists of atmolysis chamber, heat exchange chamber and gas collection chamber. The input interface of pyrolysis gas is provided in the atmolysis chamber. The input interface and output interface of syngas are provided in the heat change chamber. The output interface of pyrolysis gas is provided in the gas collection chamber. The waste storage pit (2) is constantly connected with the sorting machine (3) through the crane grab (1). The sorting machine (3) is constantly connected with a feed inlet of the $CO_2$ gas sealed feeding means (13) of plasma gasification equipment by the belt conveyor or screw feeders. The outlet of $CO_2$ gas sealed feeding means (13) is connected to the inlet of plasma gasifier (23). The pyrolysis gas outlet of the plasma gasifier (23) is connected to the input interface of pyrolysis gas of the heat exchanger b (21) through the circulating fan (18). The output interface of pyrolysis gas of the heat exchanger b (21) is connected to the input interface of pyrolysis gas in the gasification section of the plasma gasifier (23). The output interface of syngas of the plasma gasifier (23) is connected to the input interface of syngas of the heat exchanger b (21). The output interface of syngas of the heat exchanger b (21) is connected to the input interface of syngas of the waste heat boiler (27). The output interface of syngas of the waste heat boiler (27) is connected to the input interface of syngas of the absorption reactor (32). The output interface of syngas of the absorption reactor (32) is connected to the mixture input interface of syngas of the cyclone duster (31). The solid substance outlet of the cyclone duster (31) is connected to the connecting pipe of syngas input interface of the absorption reactor (32). The solid gaseous substance outlet of the cyclone duster (31) is connected to the syngas input interface of the bag dust collector (38). The output interface of syngas of the bag dust collector (38) is connected to the induction port of a compressor a (44). The exhaust port of the compressor a (44) is connected to the input interface of a syngas storage tank (48). The output interface of the syngas storage tank (48) is connected to the input interface of a hydrogenation mixer (49). The output interface of syngas of the hydrogenation mixer (49) is connected to the suction inlet of a compressor i (51). The exhaust port of the compressor i (51) is connected to the virgin gas port of a methanol synthesis reactor (52). The methanol gas outlet of the methanol synthesis reactor (52) is connected to a methanol gas inlet of the mixed absorber (55). The mixture outlet of the mixed absorber (55) is connected to the mixture input interface of a distillation column (62). The unreacted gas outlet of the distillation column (62) of is connected to the return-air interface of the methanol synthesis reactor (52) via an unreacted gas pipeline (61) and the compressor b (56). The methanol product outlet of the distillation column (62) is connected to a methanol tank (65). The limewater outlet of distillation column (62) is connected to the input interface of a decontaminator (58). The limewater outlet of the decontaminator (58) is connected to the water inlet of a circulating pump (60). The water outlet of the circulation pump (60) is connected to the limewater inlet of a mixed absorber (55). In the system described, the preprocessing device further comprises a spiral moisture expelling and feeding means (10) and the digester (9). The spiral moisture expelling and feeding means (10) is provided between a sorting machine (3) and $CO_2$ gas sealed feeding means (13). The waste material outlet of sorting machine (3) is constantly connected to the hopper of spiral moisture expelling and feeding means (10) through a belt conveyor (8). The material outlet of spiral moisture expelling and feeding means (10) is connected to the material inlet of $CO_2$ gas sealed feeding means (13) through a duct a (12). The outlet of $CO_2$ gas sealed feeding means (13) is connected to the material inlet of a plasma gasifier (23) through a duct b (14). The waste storage pit (2), a sorting machine (3) and the leachate interface of spiral moisture expelling and feeding means (10) are connected to the material inlet of the digester (9). The biogas outlet of the digester (9) is connected to the gasification section of the plasma gasifier (23). An induced-draft fan (40) is also provided between a waste heat boiler (27) and an absorption reactor (32). The syngas outlet of a waste heat boiler (27) is connected to the air inlet of an induced-draft fan (40). The air outlet of the induced-draft fan (40) is connected to the syngas input interface of an absorption reactor (32). The unreacted gas pipeline (61) at the terminal end of methanol synthesis system is provided with the exhaust gas interface and the ammonia plant. Meanwhile, an exhaust feedback pipeline (30) is provided between the plasma gasifier (23) and the device at the terminal end of the methanol synthesis system. The exhaust gas interface of an unreacted gas pipeline (61) is, via a control valve, respectively connected to the exhaust feedback pipeline (30) of the plasma gasifier (23) and material inlet interface of the ammonia plant. The exhaust gas outlet of ammonia plant is connected to the exhaust feedback pipeline (30) of the plasma gasifier (23).

In the equipment of above-mentioned system: A waste heat boiler (27), an absorption reactor (32), a cyclone duster (31), a bag dust collector (38), a $CO_2$ absorber (42), a regeneration tower (46), a methanol tank (65), a distillation column (62) and a decontaminator (58) are manufactured using conventional techniques. The methanol synthesis reactor (52) can be manufactured using known technology or the technology of China Patent ZL 200710166618.5 "Electro-catalytic synthesis reactor".

An equipment of gasification-liquefaction disposal for MSW, Comprises the gasification means that consist of a plasma gasifier (23), a plasma torch (24), a circulating fan (18), a heat exchanger b (21) and connecting ducts. The plasma gasifier (23) is divided into a drying section (23-I), a pyrolysis section (23-II) and a gasification zone (23-III) from top to bottom. The drying section (23-I), pyrolysis section (23-II) and gasification zone (23-III) communicates directly. The plasma torch (24) is provided in the furnace wall of the gasification section (23-III). A waste material inlet (2302) and a pyrolysis gas outlet (2303) are provided in the upper part of the drying section (23-I). The input interface a (2309) of pyrolysis gas is provided in the gasification section (23-III). A slag hole (2307) is provided in the lower part of gasification section (23-III). An output interface a (2304) of syngas is provided in the joint position of the pyrolysis section (23-II) and gasification section (23-III). The heat exchanger b (21) consists of an atmolysis chamber (2102), a heat exchange chamber (2104), a heat exchange bundle (2105) and a gas collection chamber (2107). An atmolysis chamber (2102), a heat exchange chamber (2104) and a gas collection chamber (2107) are arranged into upper, middle and lower parts. A heat exchange chamber (2104) is in the middle. An atmolysis chamber (2102), a heat exchange chamber (2104) and a gas collection chamber (2107) are inside a steel shell. The exterior of the steel shell is covered with an insulation material. The atmolysis chamber (2102) and the heat exchange chamber (2104) are separated by an upper baffle. The heat exchange chamber (2104) and gas collection chamber (2107) are separated by a lower baffle. A heat exchange bundle (2105) is provided in the heat exchange chamber (2104), with both ends intersecting the atmolysis chamber (2102) and the gas collection chamber (2107). The atmolysis chamber (2102), bundle (2105) and gas collection chamber (2107) constitute a return passage of pyrolysis gas. The input interface b (2101) of pyrolysis gas is provided in an atmolysis chamber (2102). The heat change chamber (2104) is provided with an input interface (2108) of syngas and output interface b (2103) of syngas. The output interface (2109) of pyrolysis gas is provided in a gas collection chamber (2107). The pyrolysis gas outlet (2303) in drying section of the plasma gasifier (23) is connected to the air inlet of a circulating fan (18). The air outlet of the circulating fan (18) is connected to the input interface b (2101) of pyrolysis gas in the atmolysis chamber. The output interface (2109) of pyrolysis gas in the gas collection chamber of the heat exchanger b (21) is connected to input interface a (2309) of pyrolysis gas in the gasification section of the plasma gasifier (23). The output interface a (2304) of syngas in plasma gasifier (23) is connected to an input interface (2108) of syngas in a heat exchange chamber of the heat exchanger b (21). The gas output interface b (2103) of syngas in the heat exchange chamber of the heat exchanger b (21) is connected to a downstream device. The soot door (2110) of the heat exchanger b (21) is connected to a fly ash returning interface (2306) in the plasma gasifier (23). In this device: when a calcium oxide torch (79) is provided in a furnace wall of the plasma gasifier (23), the calcium oxide torch (79) is provided in a furnace wall of the gasification section (23-II) of the plasma gasifier (23). The calcium oxide torch (79) is provided with a $CO_2$ input interface (7901) and a calcium oxide input interface (7902). Meanwhile, a gas-solid separator (17) is provided between pyrolysis gas outlets in drying section (2303) of the plasma gasifier (23) and an air inlet of the circulating fan (18). The pyrolysis gas outlet (2303) in the drying section of the plasma gasifier (23) is connected to a mixture inlet (1702) of a gas-solid separator (17). The gaseous material outlet (1703) of the gas-solid separator (17) is connected to the air inlet of the circulating fan (18). The solid material outlet (1701) of the gas-solid separator (17) is connected to the input interface of calcium oxide (7902) of the calcium oxide torch (79). The $CO_2$ input interface (7901) of the calcium oxide torch (79) is connected to the $CO_2$ gas pipeline. The gasification section (23-III) of the plasma gasifier (23) is also provided with a fly ash returning interface (2306), a biogas input interface (2308) and an exhaust gas input interface (2305). The heat exchange chamber (2104) of the heat exchanger b (21) is also provided with a soot-blowing opening (2106) and a soot door (2110). The soot door (2110) of the heat exchanger b (21) is connected to the fly ash returning interface (2306) in the plasma gasifier (23). The soot-blowing opening (2106) of the heat exchanger b (21) is connected to a soot-blowing fan. The air inlet of soot-blowing fan is connected to the syngas pipeline. The air outlet of soot-blowing fan is connected to a soot-blowing opening (2106) of the heat exchanger b (21).

The beneficial effect of the present invention is the gasification-liquefaction disposal for MSW can realize zero emissions and avoid dioxin contamination. No pollutant is released throughout the disposal process and the produced methanol products can be used as chemical raw materials or industrial fuel. The economic benefits obtained are much higher than waste incineration power. Waste incineration produces large amount of carbon dioxide gas and other pollutant emissions, harming the environment severely. The technology of the present invention does not emit smoke and does not pollute the environment. Waste incineration will inevitably produce highly toxic dioxin that is difficult to eliminate and is harmful to human health when the flue gas is released to the atmosphere. The present invention can inhibit the formation of dioxin. Even if an extremely small amount of dioxin appears, it is also easy to clear by purification equipment at a terminal end. Compared with waste landfill disposal, the technology of the present invention does not release any pollutants and greenhouse gases. Waste landfill disposal transfers the pollution to underground, emits large quantities of greenhouse gases, contaminates soil and groundwater, endangering the health of the human body and also affecting the next generations of human being. The present invention utilizes waste as a resource to produce clean energy, reduce energy pressure and meanwhile generate economic benefits. After the disposal is commercialized, government will not bear any cost. The waste landfill is not only a waste of resources, but also a bottomless pit for its cost, giving a large financial pressure on government. The land occupied by the technology of the present invention is much less than waste landfill. The present invention is suitable for harmless resource disposal of municipal solid waste, rural solid waste, medical waste, industrial high polymer waste, agricultural and forestry wastes, composting remainder and waste in waste sorting sites.

Figure 1:
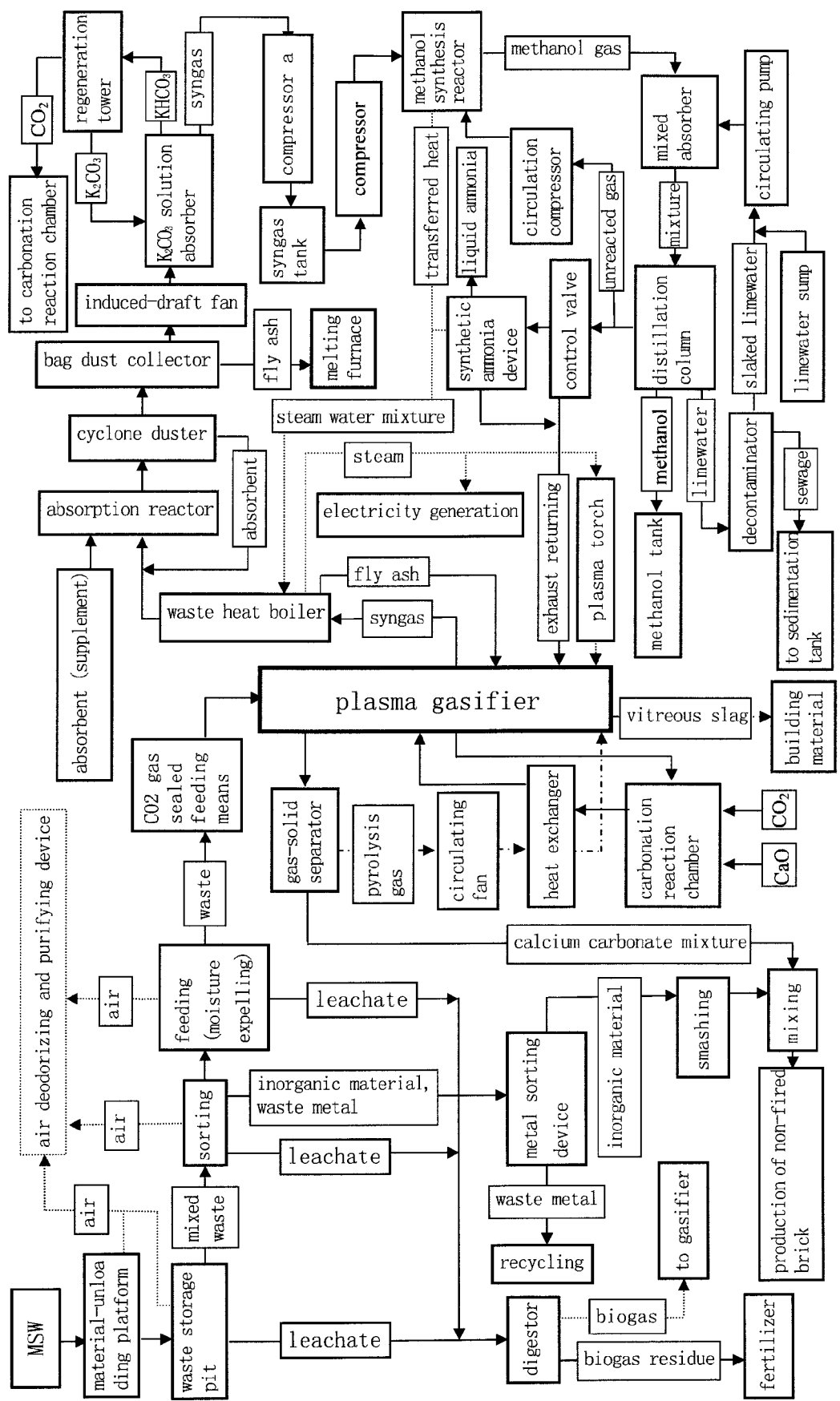
FIG. 1 is a process flow diagram of gasification-liquefaction disposal for MSW of the present invention.

In the figure: 1. crane grab, 2. waste storage pit, 3. sorting machine, 4. inorganic material silo, 5. belt conveyer, 6. magnetic separator, 7. waste metal silo, 8. belt conveyer, 9. digestor, 10. spiral moisture expelling and feeding means, 11. biogas pipeline, 12. waste duct a, 13. gas sealed feeding means, 14. waste duct b, 15. air pump, 16. material-blowing fan, 17. gas-solid separator, 18. circulating fan, 19. interface of calcium oxide supplementation, 20. heat exchanger a, 21. heat exchanger b, 22. air pipe, 23. plasma gasifier, 24. plasma torch, 25. high-temperature deodorizer, 25'. air deodorizing and purifying device, 26. heat exchanger c, 27. waste heat boiler, 28. syngas pipeline, 29. fly ash pipeline, 30. exhaust feedback pipeline, 31. cyclone duster, 32. absorption reactor, 33. absorbent silo, 34. material-blowing fan, 35. melting kiln, 36. absorbent circulating pipe, 37. absorbent feedback pipe, 38. bag dust collector, 39. material-blowing fan, 40. induced-draft fan, 41. CO shift reactor, 42. $CO_2$ absorber, 43. supplementing pipe of absorption solution, 44. compressor a, 45. circulating pipe of absorption solution, 46. regeneration tower, 47. circulating pump of absorption solution, 48. syngas tank, 49. hydrogenation mixer, 50. supplementing interface of hydrogen gas, 51. compressor i, 52. methanol synthesis reactor, 53. sedimentation tank, 54. water pump, 55. mixed absorber, 56. compressor b, 57. condenser, 58. decontaminator, 59. solidified slag, 60. circulating pump, 61. unreacted gas pipeline, 62. distillation column, 63. synthetic ammonia reactor, 64. compressor c, 65. methanol tank, 66. condensor, 67. ammonia separator, 68. liquid ammonia tank, 69. air pump, 70. waste leachate pool, 71. water pump, 72. air curtain, 73. material-unloading platform, 74. exhaust fan, 75. control valve, 76. control valve, 77. control valve, 78. control valve, 79. calcium oxide torch 301. hopper, 302. inorganic material outlet, 303. waste outlet, 901. taphole, 902. biogas outlet, 903. feed inlet, 1001. driving shaft, 1002. hopper, 1003. spiral shaft, 1004. spiral shell, 1301. feed inlet, 1302. $CO_2$ supplementing interface, 1303. $CO_2$ gas seal, 1304. storage silo, 1305. spiral shell, 1306. spiral shaft, 1307. driving shaft, 1701. solid material outlet, 1702. mixed material outlet, 1703. gaseous material outlet, 2001. input interface of pyrolysis gas, 2002. atmolysis chamber, 2003. input interface of heat carried gas, 2004. output interface of pyrolysis gas, 2005. gas collection chamber, 2006. heat exchange chamber, 2007. carbonation reaction chamber, 2008. $CO_2$ input interface, 2009. calcium oxide torch, 2010. output interface of heat carried gas, 2101. input interface of pyrolysis gas b, 2102. atmolysis chamber, 2103. syngas output interface, 2104. heat exchange chamber, 2105. heat exchange bundle, 2106. soot-blowing opening, 2107. gas collection chamber, 2108. syngas input interface, 2109. output interface of pyrolysis gas, 2110. soot door, 2301. inlet of heat carried gas, 2302. inlet of waste material, 2303. outlet of pyrolysis gas, 2304. syngas output interface, 2305. exhaust input interface, 2306. fly ash feedback interface, 2307. taphole, 2308. biogas input interface, 2309. a input interface a of pyrolysis gas, 2310. output interface of heat carried gas, 2311. furnace wall, 23-I. drying section, 23-II. pyrolysis section, 23-III. gasification section, 2501. input interface of air odor, 2502. syngas outlet, 2503. outlet of deodored air, 2504. syngas input interface, 2601. air outlet, 2602. hot air inlet, 2701. syngas inlet, 2702. syngas outlet, 3101. gaseous material outlet, 3102. input interface of mixed material, 3103. solid material outlet, 3201. syngas outlet, 3202. input interface of absorbent, 3203. input interface of syngas, 3801. syngas output interface, 3802. fly ash outlet, 3803. syngas input interface, 4101. syngas input interface, 4102. syngas output interface, 4201. syngas output interface, 4202. syngas input interface, 4203. $K_2CO_3$ input interface of $K_2CO_3$ solution, 4204. $KHCO_3$ input interface of $KHCO_3$, 4601. $KHCO_3$ output interface of $KHCO_3$, 4602. $K_2CO_3$ output interface of $K_2CO_3$ solution, 4603. output interface of $CO_2$, 4801. syngas input interface, 4802. syngas output interface, 4901. input interface of hydrogen gas, 4902. syngas output interface, 4903. syngas input interface, 5201. material gas inlet, 5202. returned gas interface, 5203. output interface of methanol gas, 5301. sewage inlet, 5302. suction pipe, 5203. slag tapping, 5501. methanol gas inlet, 5502. limewater inlet, 5503. mixture inlet, 5701. limewater outlet, 5702. limewater inlet, 5801. limewater outlet, 5802. sewage outlet, 5803. input interface of limewater, 6201. input interface of mixture, 6202. limewater outlet, 6203. outlet of methanol product, 6204. outlet of unreacted gas, 6301. material inlet, 6302. ammonia outlet, 6601. input interface of ammonia, 6602. output interface of ammonia mixture, 6701. input interface of ammonia mixture, 6702. output interface of liquid ammonia, 6703. exhaust outlet, 7901. $CO_2CO_2$ input interface, 7902. input interface of calcium oxide.

Figure 4:
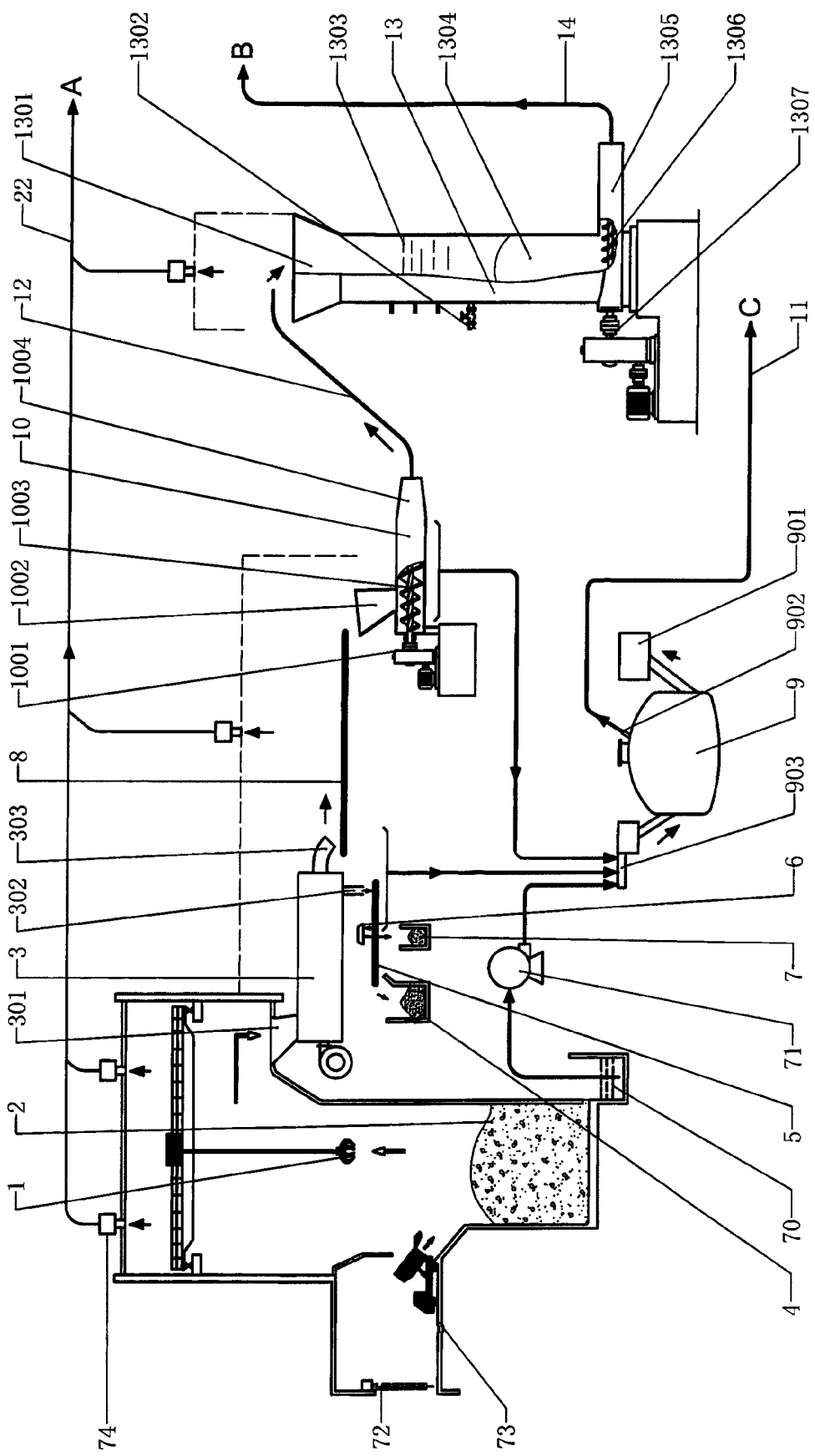
FIG. 4 is the detailed part of zone I in FIG. 2 or the detailed part in zone I of FIG. 3.
Figure 5:
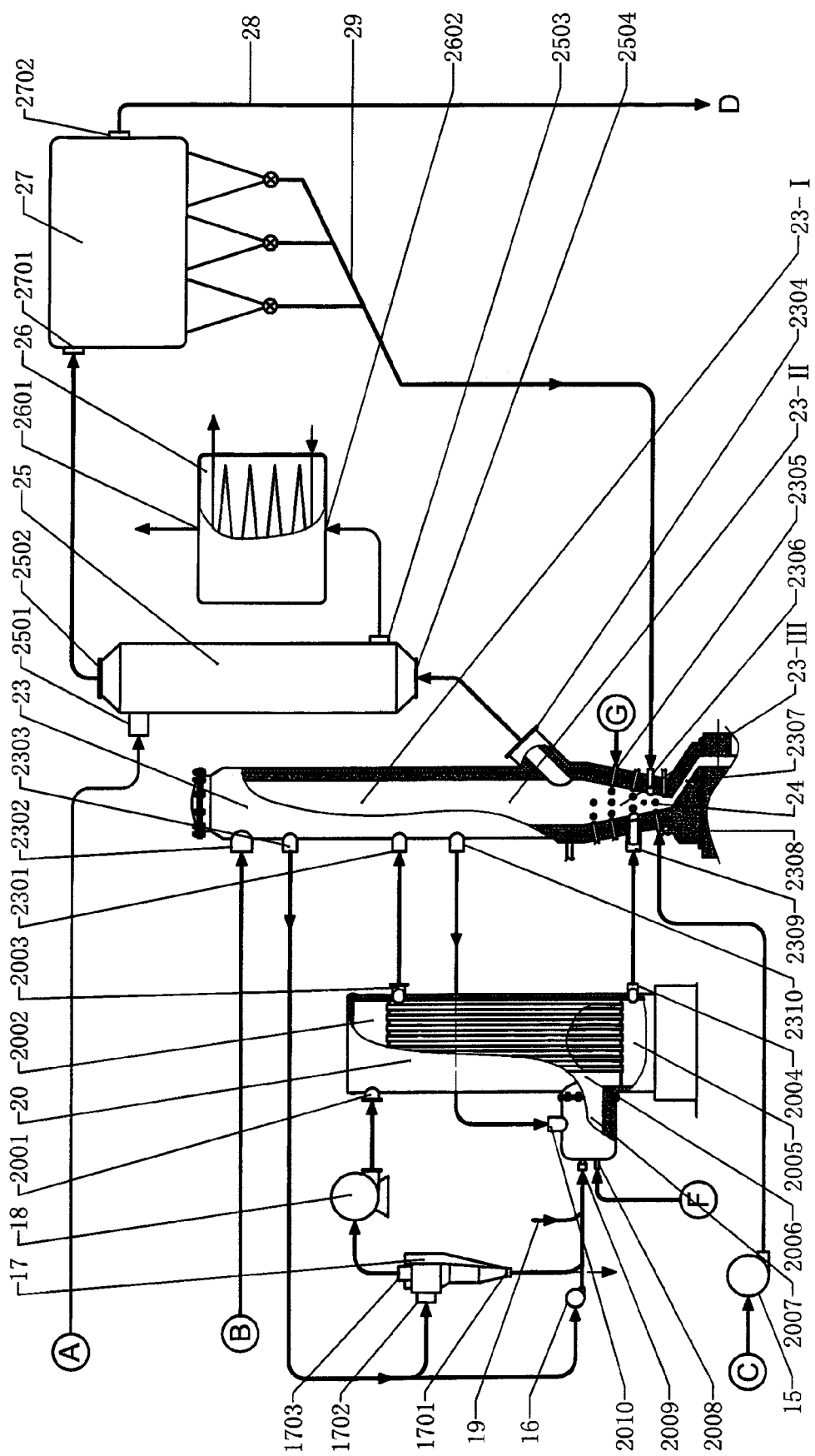
FIG. 5 is the detailed part of zone II-a in FIG. 2.
Figure 6:
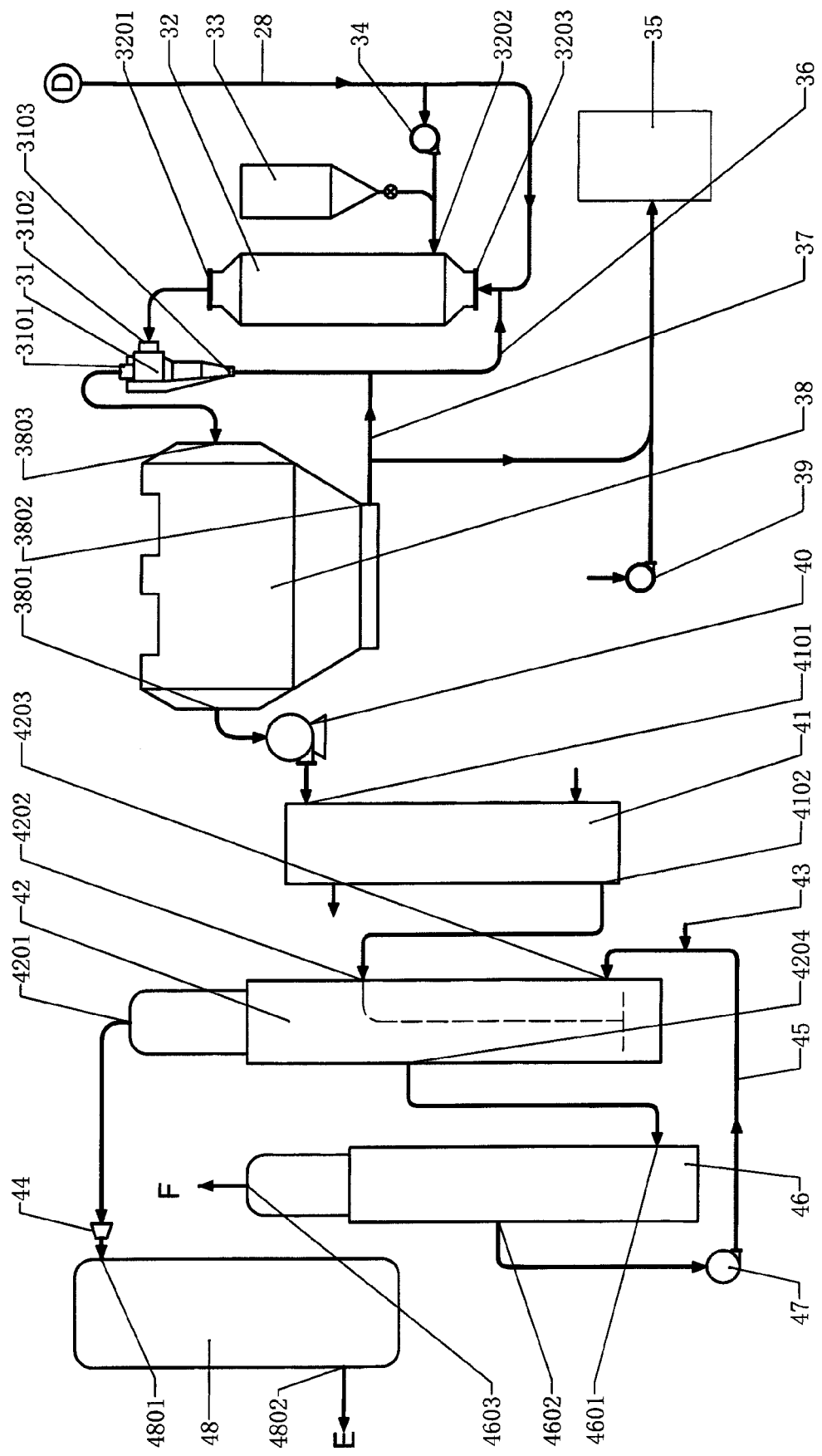
FIG. 6 is the detailed part of zone III-a in FIG. 2.
Figure 7:
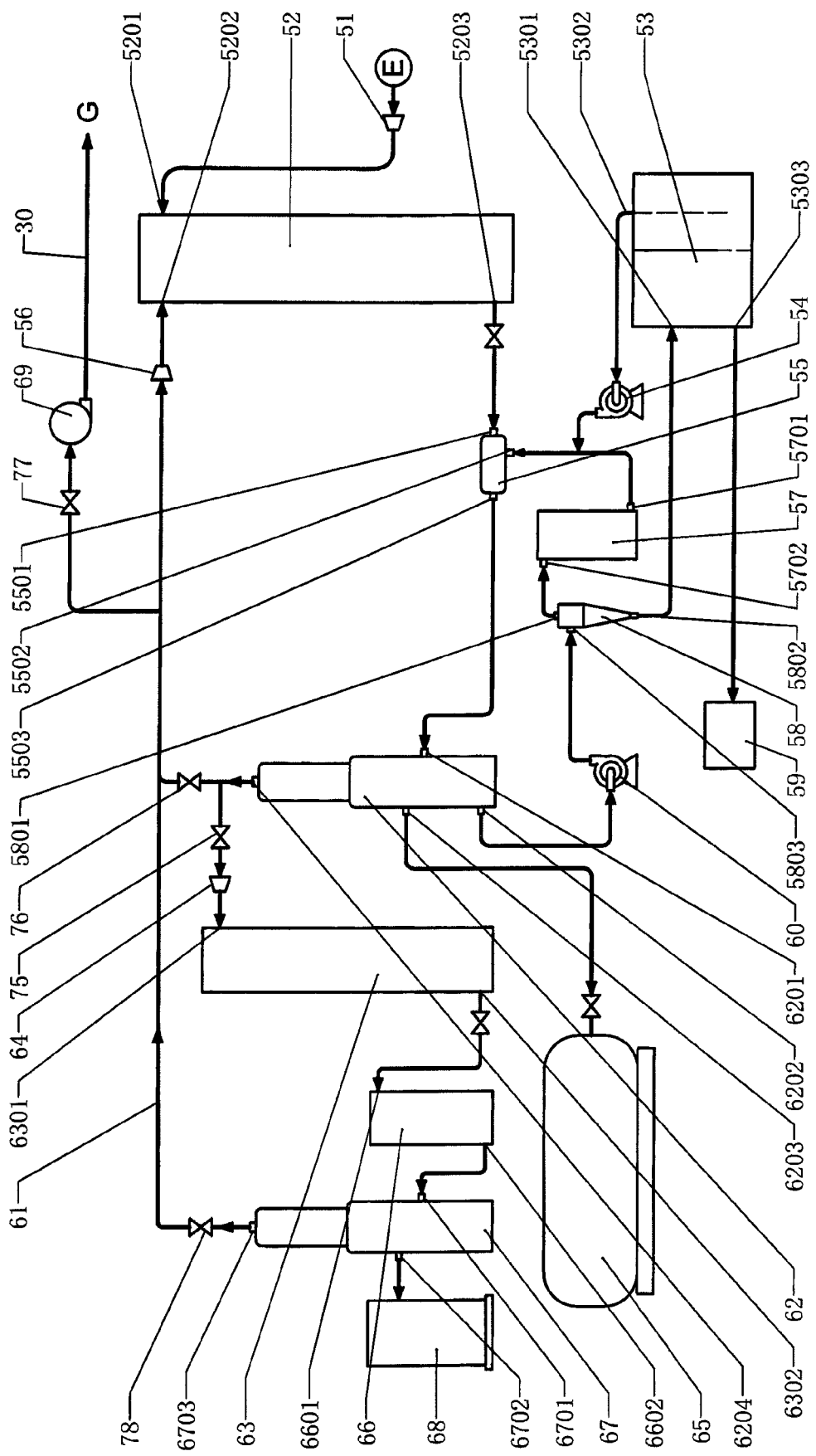
FIG. 7 is the detailed part of zone IV in FIG. 2 or the detailed part in zone IV of FIG. 3.

In FIG. 4, 5, 6, 7, 8, 9, 10: A is correspondingly connected to the Ⓐ; B is correspondingly connected to the Ⓑ; C is correspondingly connected to Ⓒ; D is correspondingly connected to Ⓓ; E is correspondingly connected to Ⓔ; F is correspondingly connected to Ⓕ; H is correspondingly connected to Ⓗ; J is correspondingly connected to Ⓙ.

DETAILED DESCRIPTION OF THE PREFERRED EMBODIMENTS

Example 1

In the embodiment shown in FIG. 1, MSW or organic waste in the waste storage pit was dehydrated to some extent by the way of fermentation, and then through separation organic matter waste separated was fed into a spiral moisture expelling and feeding means. In the process of conveying through the screw feeder, some amount of water was removed further by extrusion. Then the waste material was fed into a plasma gasifier through a $CO_2$ gas sealed device. The MSW, after dried in drying section of plasma gasifier and pyrolyzed in pyrolysis section of plasma gasifier, became MSW carbon and entered the gasification section for gasification reaction with the decomposer of the water steam injected into the gasification section from a plasma torch, and completed gasification and generates hydrogen-rich syngas in which CO and $H_2$ are the main components. The operating temperature of drying section was at between 120 to 300° C.; the operating temperature of pyrolysis section is between 300 to 1000° C.; the operating temperature of gasification section is at between 1000 to 1300° C.; the operating temperature of melted slag zone is at between 1300 to 1600° C.; the operating pressure in the gasification furnace is controlled at between 0~5 kPa. A plasma torch is provided in the gasification section, and the heat required by the gasification in the furnace is mainly provided by the plasma torch and the exothermic reaction of plasma active chemicals and MSW carbon. As the working steam for gasifying agent and the plasma torch, the water steam is heated to >4200° C. by the plasma torch, so that water molecules are decomposed completely, generating $H^*$, $H_2^*$, $HO^*$, $O^*$, $O_2^*$ and $H_2O^*$ that are then directly sprayed on the MSW carbon in the gasification section. The MSW carbon serves for hydrogen and oxygen absorber to generate CO and $H_2$. Clinker is melted to a liquid slag at 1300~1600° C. environment in melted slag zone of the furnace, and discharges via a water seal to the slag pool and becomes vitreous grains. The heat emitted when calcium oxide absorbs $CO_2$ to produce calcium carbonate is provided as an assistant heat source for gasification and an assisting plasma gasification. A carbonization reaction chamber is provided in the gasification system. Calcium oxide and $CO_2$ were inputted into the carbonization reaction chamber for carbonization reaction. Calcium oxide also serves for dechlorinator or desulfurizer that introduces the pyrolysis gas generated in pyrolysis section of the plasma gasifier into the carbonation reaction chamber. In the environment of the existence of excessive 1.2 times calcium oxide, dioxin precursors, chlorides and sulfides were removed. Then pyrolysis gas was also used as a carrier gas to carry calcium oxide, calcium carbonate mixture and heat into the drying section of the plasma gasifier, thus providing heat for the drying and preheating of the new materials into the furnace waste. Then the pyrolysis gas was led out of the furnace and into the gas-solid separator to separate calcium oxide and calcium carbonate. Then pyrolysis gas was fed into the heat exchanger by the circulation fan, and after indirect heating in the heat exchanger, fed into the gasification section of the plasma gasifier. In the environment of 1000 to 1300° C., methane, gaseous tar, ethylene, ethane, water steam, etc. in pyrolysis gas were pyrolyzed and chemically reacted. In addition, dioxin was thoroughly disintegrated. By circulated gasification, the waste in the furnace was completely decomposed, and produced a hydrogen-rich syngas in which hydrogen and carbon monoxide were main components. The hydrogen-rich syngas was led from the plasma gasifier into a waste heat boiler to recover waste heat to produce steam. Meanwhile the syngas cooled down to about 232° C. and after cooling through exhaust heat boiler was fed to absorption reactor for deacidification. With calcium oxide or calcium hydroxide as the absorbent, chlorides, sulfides, fluorides, and other acidic pollutants were removed from the syngas. Then through the cyclone duster, the absorber was separated and returned to the absorption reactor for recycling. Then the syngas removed fly ash by using bag dust collector. After deacidification and dedusting, the syngas was fed to a $CO_2$ absorber to absorb carbon dioxide in the syngas with potassium carbonate solution, then the potassium bicarbonate generated by potassium carbonate solution absorbing carbon dioxide was fed to a regeneration reactor. By heating, potassium bicarbonate was decomposed into potassium carbonate solution and carbon dioxide. The decomposed potassium carbonate solution was returned to $CO_2$ absorbing tower for recycling and the decomposed carbon dioxide was fed to carbonation reaction chamber for carbonation reaction. The syngas after removing carbon dioxide was fed into a syngas tank through compressor a. Out of the syngas tank, syngas was fed through the compressor to a methanol synthesis reactor to produce methanol. The hydrogen-rich syngas was catalyzed and synthesized to methanol product in the methanol synthesis reactor. Then the methanol gas was fed to a mixed absorber to mix with limewater, so that the residual contaminants including dioxin and carbon dioxide was absorbed by lime. Then through distillation, methanol was separated and the unreacted gas was returned to the methanol synthesis reactor for recycling reaction. Limewater after decontamination was fed back to mixed absorber for recycling use by a circulating pump. The exhaust was fed by a control valve to the plasma gasifier for recycling or synthetic ammonia equipment to produce liquid ammonia to remove nitrogen gas and form a closed loop production system. In this embodiment, the leachate generated in MSW pretreating process was fed into a digester to produce biogas by anaerobic fermentation. The biogas was fed into the plasma gasifier for decomposition and the biogas residue was used as fertilizer. Selected inorganic materials sorted in the pretreatment process were resorted for scrap metal recycling. Then non-metallic inorganic materials were ground and mixed with calcium carbonate, calcium oxide separated from the gasification system to produce non-fired bricks. The slag discharged from plasma gasifier into water sealed slag pool became vitreous particles that can be directly used as building material. The fly ash collected from the bag filter was then treated through melting kiln and the slag can be directly used as building material. The steam water mixture removed from the methanol synthesis reactor was fed into the waste heat boiler to produce steam that can serve as working steam for plasma torch and steam power generation. In the present embodiment, when the fractional ratio of hydrogen in the syngas produced in the plasma gasifier was not up to the requirements of methanol synthesis, add an operation of carbon monoxide conversion in the previous stage of $CO_2$ absorbing tower to increase the proportion of hydrogen in the syngas, or conduct hydrogenation to meet the requirements of syngas. Methanol synthesis can use conventional synthesis reactor or the electro-catalytic synthesis reactor specified in Chinese Patent No. 200710166618.5. When using conventional synthesis reactor, the synthesis of methanol uses Cu/Zn/Al catalyst at operating pressure of 3 to 15 Mpa and at operating temperature of 210 to 280° C. When using electro-catalytic synthesis reactor, the synthesis of methanol uses Cu/Zn/Al catalyst at operating pressure of 0~1 Mpa and at operating temperature 120 to 400° C.

Example 2

Figure 2:
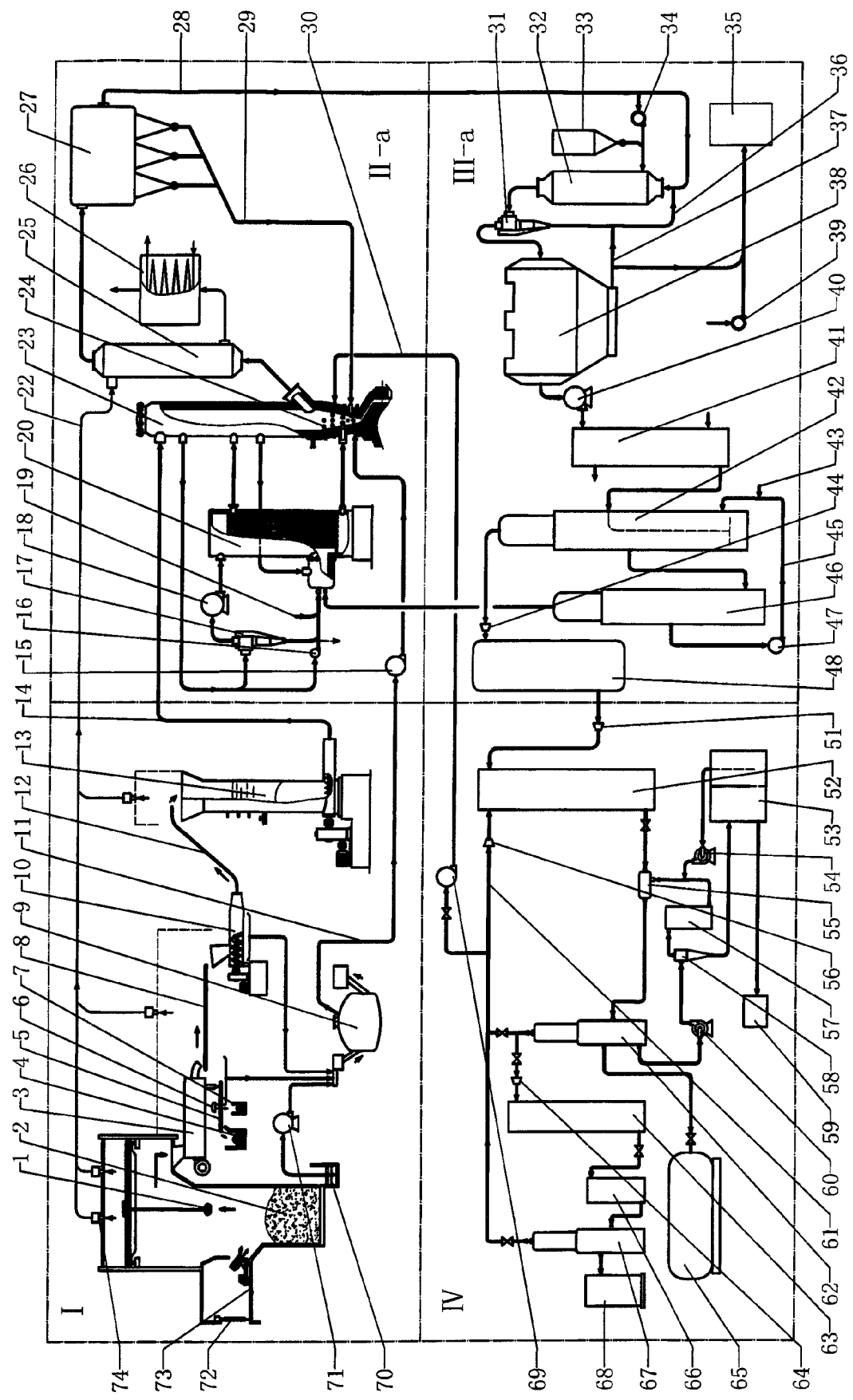
FIG. 2 is a system diagram of calcium oxide assisted gasification-liquefaction disposal for MSW of the present invention.

As shown in the system diagram of FIG. 2 and detailed drawings in FIGS. 4, 5, 6, 7 of the present invention, a MSW gasification-liquefaction disposal system comprises: a MSW pretreating zone (zone I in FIG. 2), a plasma gasification zone (zone II-a of FIG. 2), a syngas purification zone (zone III-1 of FIG. 2) and a zone of methanol synthesis and a terminal purification zone (zone IV of FIG. 2). The system comprises a material-unloading platform (73), a waste storage pit (2), a crane grab (1), a sorting machine (3), spiral moisture expelling and feeding means (10), $CO_2$ gas sealed feeding means (13), a plasma gasifier (23), a plasma torch (24), a gas-solid separator (17), a circulating fan (18), a carbonation reaction chamber (2007), a heat exchanger (20), a waste heat boiler (27), an absorption reactor (32), a cyclone duster (31), a bag dust collector (38), an induced-draft fan (40), a CO shift reactor (41), a $CO_2$ absorber (42), a regeneration repercussion tower (46), a compressor a (44), a syngas tank (48), a compressor (51), a methanol synthesis reactor (52), a mixed absorber (55), a distillation column (62), a compressor b (56), a methanol output tank (65), an asynthetic ammonia reactor (63) and connecting ducts. Among which: the material-unloading platform comprise an unloading lane and a vehicle command room; an unloading lane, a vehicle command room, a waste storage pit (2) and a crane grab (1) were provided in steel-concrete structure buildings; An air curtain was provided in the entrance of garbage truck in these buildings. An air outlet of exhaust fan (74) on the roof was connected to input interface of air odor (2501) of high-temperature deodorizer (25) through air pipe (22). An outlet of deodored air (2503) of high-temperature deodorizer (25) was connected to an hot air inlet (2602) of the heat exchanger c (26). Spiral moisture expelling and feeding means (10) consisted of a hopper (1002), a driving shaft (1001), a spiral shaft (1003) and a spiral shell (1004). The hopper (1002) was provided over a spiral shell (1004). The spiral shell (1004) is therein provided with a spiral shaft (1003) that can perform rotation, water squeezing and material pushing with a driving shaft (1001). The material outlet of spiral moisture expelling and feeding means (10) is provided in the front end of spiral shell (1004). $CO_2$ gas sealed feeding means (13) consists of a storage silo (1304), a $CO_2$ gas seal (1303), a spiral shell (1305), a spiral shaft (1306), a driving shaft (1307), a transmission case and a motor. A storage silo (1304) is provided over a spiral shell (1305) and with $CO_2$ gas sealed material. The material outlet of storage silo (1304) communicates with the material inlet of a spiral shell (1305). The spiral shell (1305) is therein provided with the spiral shaft (1306) that performs the function of material pushing. The material outlet of $CO_2$ gas sealed feeding means (13) is in the front end of a spiral shell (1305). The inner space of plasma gasifier (23) is divided into the drying section (23-I), the pyrolysis section (23-II) and the gasification section (23-III); The drying section (23-I) is provided with an inlet of waste material (2302), an inlet of heat carried gas (2301) and an outlet of pyrolysis gas (2303). The pyrolysis section (23-II) is provided with output interface of the heat carried gas (2310) and the gasification section (23-III) is provided with input interface a of pyrolysis gas (2309). A taphole (2307) is provided in the bottom of gasification section (23-III) and a melted slag zone is provided between the gasification section (23-III) and taphole (2307). Syngas output interface a (2304) is provided in the joint position between the pyrolysis section (23-II) and gasification section (23-III). A plasma torch (24) is provided in gasification section (23-III) in the lower part of the plasma gasifier (23). A heat exchanger a (20) consists of an atmolysis chamber (2002), a heat exchange chamber (2006) and a gas collection chamber (2005). The input interface (2001) of pyrolysis gas is provided in the atmolysis chamber (2002). The output interface (2003) of heat carried gas is provided in the heat change chamber (2006). The output interface (2004) of pyrolysis gas is provided in the gas collection chamber (2005). The carbonation reaction chamber (2007) is installed over the heat exchanger a (20). The carbonation reaction chamber (2007) communicates with the heat exchange chamber (2006) of the heat exchanger a (20). The carbonation reaction chamber (2007) is provided with the input interface (2010) of heat carried gas, calcium oxide torch (2009) of calcium oxide input interface (2008). The mixing absorber (55) consists of a mixed absorbing chamber, a Venturi water inlet, a methanol gas nozzle, a methanol gas inlet (5501), a limewater inlet (5502), a mixture inlet (5503) and the shell. The mixing absorbing chamber, Venturi water inlet and methanol gas nozzle are inside the shell. The mixing absorbing chamber is positioned after the Venturi water inlet, and methanol gas nozzle is positioned is before the Venturi inlet. The diameter of methanol gas nozzle gradually expands from spout to inlet. The length of methanol gas nozzle is 2.5 times the average diameter. The outer diameter of an orifice of a methanol gas nozzle is 0.7 to 0.8 times the inner diameter of Venturi water inlet. The methanol gas nozzle and Venturi water inlet are coaxially designed and the methanol gas nozzle extends the ⅓ length into the Venturi water inlet in the shell. A methanol gas inlet (5501) is connected to the inlet of methanol gas nozzle. A limewater inlet (5502) is provided in the shell between the Venturi water inlet and input interface of methanol gas. The mixture inlet (5503) is provided in the shell of mixed absorbing chamber. The waste storage pit (2) is constantly connected to a hopper (301) of a sorting machine (3) through a crane grab (1). The waste outlet (303) of a sorting machine (3) is constantly connected to the hopper (1002) of spiral moisture expelling and feeding means (10) through a belt conveyer (8). The material outlet of spiral moisture expelling and feeding means (10) is constantly connected to the material inlet of $CO_2$ gas sealed feeding means (13) through duct a (12). The material outlet of $CO_2$ gas sealed feeding means (13) is connected to waste material inlet of plasma gasifier (23) through duct b (14). The output interface (2310) of heat carried gas of the plasma gasifier (23) is connected to the input interface (2010) of the heat carried gas of a carbonation reaction chamber (2007). The output interface (2003) of heat carried gas of heat exchanger a (20) is connected to the inlet (2301) of heat carried gas of the plasma gasifier (23). The outlet (2303) of heat carried gas of the plasma gasifier (23) is connected to the mixture inlet (1702) of the gas-solid separator (17). The gaseous substance outlet (1703) of the gas-solid separator (17) is connected to the input interfaces (2001) of pyrolysis gas of heat exchanger a (20) through circulating fan (18). The output interface (2004) of pyrolysis gas of heat exchanger a (20) is connected to the input interface a (2309) of pyrolysis gas of the plasma gasifier (23). The solid material outlet (1701) of the gas-solid separator (17) is respectively connected to slag silo and calcium oxide torch (2009) through ducts. The interface of calcium oxide supplementation (19) and material-blowing fan (16) are provided in connecting ducts. The output interface a (2304) of syngas of the plasma gasifier (23) is connected to the syngas inlet (2701) of the waste heat boiler (27). The water supplementation interface of the waste heat boiler (27) is connected to water supplying equipment. The steam output interface of the waste heat boiler (27) is connected to steam supply pipe network. The soot door (29) of the waste heat boiler (27) is connected to fly ash returning interface (2306) in the plasma gasifier (23) through fly ash pipeline (29). The syngas outlet (2702) of the waste heat boiler (27) is connected to syngas input interface (3203) of the absorption reactor (32). The material outlet of the absorbent silo (33) is connected to absorbent input interface (3202) of the absorption reactor (32). The material pipe of absorbent input interface (3202) is also connected to the air outlet of the material-blowing fan (34). The air inlet of the material-blowing fan (34) is connected to the syngas pipeline (28). The syngas output interface (3201) of the absorption reactor (32) is connected to the mixture input interface (3102) of the cyclone duster (31). The solid substance outlet (3103) of the cyclone duster (31) is connected to the connecting ducts of the input interface (3203) of the absorption reactor (32). The solid gaseous substance outlet (3101) of the cyclone duster (31) is connected to the syngas input interface (3803) of the bag dust collector (38). The fly ash outlet (3802) of the bag dust collector (38) is connected to a melting kiln (35). The syngas output interface (3801) of the bag dust collector (38) is connected to the air inlet of the induced-draft fan (40). The air outlet of induced-draft fan (40) is connected to syngas input interface (4101) of the CO shift reactor (41). The syngas output interface (4102) of the CO shift reactor (41) is connected to the syngas input interface (4202) of the $CO_2$ absorbing tower (42). The output interface (4204) of $KHCO_3$ of the $CO_2$ absorbing tower (42) is connected to the input interface (4601) of $KHCO_3$ of the regeneration tower (46). The $CO_2$ output interface (4603) of the regeneration tower (46) is connected to the input interface (2008) of $CO_2$ of the carbonation reaction chamber (2007). The output interface (4602) of K₂CO₃ solution of the regenerating tower (46) is connected to the input interface (4203) of K₂CO₃ solution of the CO₂ absorbing tower (42). Syngas output interface (4201) of the CO₂ absorbing tower (42) is connected to syngas input interface (4801) of syngas tank through compressor a (44). Syngas output interface (4802) of the syngas storage tank (48) is connected to the suction port of the compressor i (51). The exhaust outlet of the compressor i (51) is connected to the material gas inlet (5201) of the methanol synthesis reactor (52). The methanol gas outlet (5203) of the methanol synthesis reactor (52) is connected to methanol gas inlet (5501) of the mixed absorber (55) through a decompression control valve. The mixture outlet (5503) of mixed absorber (55) is connected to mixture input interface (6201) of distillation column (62). Unreacted gas outlet (6204) of distillation column (62) is connected to the return-air interface (5202) of methanol synthesis reactor (52) through a control valve (76), unreacted gas pipeline (61) and compressor b (56). The methanol product outlet (6203) of the distillation column (62) is connected to the methanol tank (65). The limewater outlet (6202) of distillation column (62) is connected to the input interface (5803) of decontaminator (58). Sewage outlet (5802) of decontaminator (58) is connected to sedimentation tank (53). The limewater outlet (5801) of decontaminator (58) is connected to the water inlet of circulating pump (60). The water outlet of the circulation pump (60) is connected to the limewater inlet (5502) of a mixed absorber (55). Suction pipe (5302) is connected to the water inlet of water pump (54) in one side of sedimentation tank (53). The water outlet of water pump (54) is connected to the connecting ducts of limewater inlet (5502) of the mixed absorber (55). Unreacted gas outlet (6204) of distillation column (62) is connected to material inlet (6301) of the synthetic ammonia reactor (63) through the control valve (75) and the compressor c (64). Ammonia outlet (6302) of the synthetic ammonia reactor (63) is connected to the ammonia gas input interface (6601) of the condenser (66). Output interface of ammonia mixture (6602) of the condenser (66) is connected to input interface of ammonia mixture (6701) of ammonia separator (67). Output interface of liquid ammonia (6702) of the ammonia separator (67) is connected to liquid ammonia tank. Exhaust outlet (6703) of the ammonia separator (67) is connected to unreacted gas pipeline (61) through the control valve (78). Unreacted gas pipeline (61) is connected to exhaust input interface (2305) of plasma gasifier (23) through the control valve (77), the air pump (69) and exhaust feedback pipeline (30). The leachate interfaces of the waste storage pit (2), sorting machine (3) and spiral moisture expelling and feeding means (10) are connected to the material inlet of digester (9) through ducts. Biogas outlet (902) of the digester (9) is connected to biogas input interface (2308) of the plasma gasifier (23) through the biogas pipeline (11) and air pump (15).

Example 3

Figure 3:
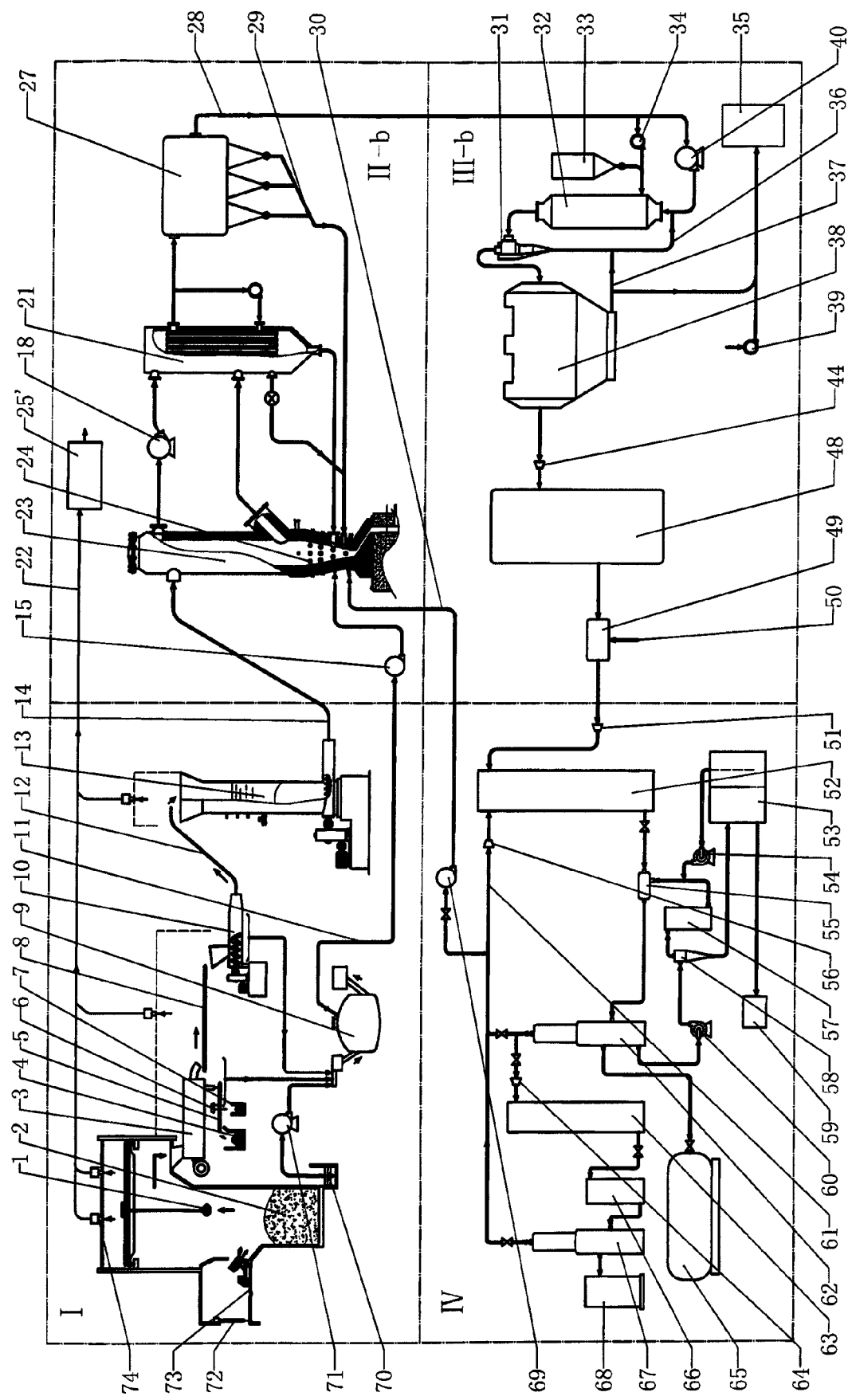
FIG. 3 is a system diagram of hydrogenation gasification-liquefaction disposal for MSW of the present invention.

As shown in the system diagram of FIG. 3 and detailed drawings in FIGS. 4, 7, 8, 9 of the present invention, a MSW gasification-liquefaction disposal system comprises: MSW pretreating zone (zone I in FIG. 3), a plasma gasification zone (zone II-b of FIG. 3), syngas purification zone (zone III-b of FIG. 3), a zone of methanol synthesis and terminal purification (zone IV of FIG. 3). The system comprises a material-unloading platform (73), a crane grab (1), a waste storage pit (2), a sorting machine (3), a digester (9), spiral moisture expelling and feeding means (10), CO₂ gas sealed feeding means (13), a plasma gasifier (23), a plasma torch (24), a circulating fan (18), a heat exchanger b (21), a waste heat boiler (27), an induced-draft fan (40), an absorption reactor (32), a cyclone duster (31), a bag dust collector (38), a compressor a (44), a syngas tank (48), a hydrogenation mixer (49), a compressor i (51), a methanol synthesis reactor (52), a mixed absorber (55), a decontaminator (56), a decontaminator (58), a circulating pump (60), a distillation column (62), a synthetic ammonia reactor (63), a compressor c (64), a methanol output tank (65), and connecting ducts. Of which: an exhaust fan (74) is provided over a waste storage pit (2) and a sorting machine (3), and its air outlet is connected to air deodorizing and purifying device 25' through an air pipe (22); The inner space of plasma gasifier (23) is divided into a drying section (23-I), a pyrolysis section (23-II), a gasification section (23-III); In the drying section (23-I) are provided a waste material inlet (2302) and a pyrolysis gas outlet (2303); The input interface a (2309) of pyrolysis gas is provided in the gasification section (23-III); A slag hole (2307) is provided in the bottom of gasification section (23-III); A melted slag zone is provided between and taphole (2307); An output interface a (2304) of syngas is provided the joint position of pyrolysis section (23-II) and gasification section (23-III); A plasma torch (24) is provided in gasification section (23-III) in the lower part of the plasma gasifier (23); Heat exchanger b (21) consists of atmolysis chamber (2102), heat exchange chamber (2104) and gas collection chamber (2107); Atmolysis chamber (2102), heat exchange chamber (2104) and gas collection chamber (2107) are isolated each other with baffles; Heat exchange bundle (2105) is provided in heat exchange chamber (2104) Between atmolysis chamber (2102) and gas collection chamber (2107); Atmolysis chamber (2102) is connected to gas collection chamber (2107) through heat exchange bundle (2105); The input interface b (2101) of pyrolysis gas is provided in the atmolysis chamber (2102); Heat change chamber (2104) is provided with syngas input interface (2108), syngas output interface b (2103), soot door (2110) and soot-blowing opening (2106). The output interface (2109) of pyrolysis gas is provided in the gas collection chamber (2107); Waste storage pit (2) is constantly connected to hopper (301) of sorting machine (3) through crane grab (1); The waste outlet (303) of sorting machine (3) is constantly connected to the hopper (1002) of spiral moisture expelling and feeding means (10) through belt conveyer (8); The material outlet of spiral moisture expelling and feeding means (10) is constantly connected to the material inlet of CO₂ gas sealed feeding means (13) through duct a (12); The material outlet of CO₂ gas sealed feeding means (13) is connected to waste material inlet of the plasma gasifier (23) through duct b (14); Pyrolysis gas outlet (2303) of plasma gasifier (23) is connected to the input interface b(2101) of pyrolysis gas of heat exchanger b (21) through circulating fan (18); The output interface (2109) of pyrolysis gas of heat exchanger b (21) is connected to input interface a (2309) of pyrolysis gas in the gasification section of the plasma gasifier (23); The output interface a (2304) of syngas in the plasma gasifier (23) is connected to input interface (2108) of syngas in of heat exchanger b (21); The soot door (2110) of heat exchanger b (21) is connected to fly ash returning interface (2306) in the plasma gasifier (23) through ash discharging valve; Syngas output interface b (2103) of heat exchanger b (21) is connected to syngas hole (2701) of waste heat boiler (27); The soot door (29) of the waste heat boiler (27) is connected to fly ash returning interface (2306) in plasma gasifier (23) through fly ash pipeline (29); The syngas outlet (2702) of the waste heat boiler (27) is connected to syngas input interface (3203) of absorption reactor (32) through induced-draft fan (40); The material outlet of absorbent silo (33) is connected to absorbent input interface (3202) of absorption reactor (32); The material pipe of absorbent input interface (3202) is also connected to the air outlet of material-blowing fan (34); The air inlet of material-blowing fan (34) is connected to syngas pipeline (28); Syngas output interface (3201) of absorption reactor (32) is connected to the mixture input interface (3102) of cyclone duster (31); The solid substance outlet (3103) of cyclone duster (31) is connected to input interface (3203) of absorption reactor (32); The solid gaseous substance outlet (3101) of cyclone duster (31) is connected to syngas input interface (3803) of bag dust collector (38); Fly ash outlet (3802) of bag dust collector (38) is connected to melting kiln (35); Syngas output interface (3801) of bag dust collector (38) is connected to syngas input interface (4801) of syngas tank (48) through compressor a (44); Syngas output interface (4802) of syngas storage tank (48) is connected to input interface (4903) of hydrogenation mixer (49); Hydrogen input interface (4901) of hydrogenation mixer (49) is connected to the hydrogen supplying equipment; The output interface (4902) of syngas of hydrogenation mixer (49) is connected to the suction inlet of compressor i (51); The exhaust outlet of the compressor i (51) is connected to material gas inlet (5201) of methanol synthesis reactor (52); The methanol gas outlet (5203) of the methanol synthesis reactor (52) is connected to methanol gas inlet (5501) of the mixed absorber (55) through a decompression control valve; The mixture outlet (5503) of a mixed absorber (55) is connected to mixture input interface (6201) of distillation column (62); Unreacted gas outlet (6204) of distillation column (62) is connected to the return-air interface (5202) of a methanol synthesis reactor (52) through a control valve (76), a unreacted gas pipeline (61) and a compressor b (56); The methanol product outlet (6203) of the distillation column (62) is connected to methanol tank (65); The limewater outlet (6202) of the distillation column (62) is connected to the input interface (5803) of decontaminator (58); Sewage outlet (5802) of the decontaminator (58) is connected to the sedimentation tank (53); The limewater outlet (5801) of the decontaminator (58) is connected to the water inlet of the circulating pump (60); The water outlet of the circulation pump (60) is connected to the limewater inlet (5502) of mixed absorber (55); Unreacted gas outlet (6204) of the distillation column (62) is connected to a material inlet (6301) of the synthetic ammonia reactor (63) through a control valve (75) and a compressor c (64); an ammonia outlet (6302) of the synthetic ammonia reactor (63) is connected to the ammonia gas input interface (6601) of the condenser (66); an output interface of ammonia mixture (6602) of the condenser (66) is connected to input interface of ammonia mixture (6701) of the ammonia separator (67); Output interface of liquid ammonia (6702) of the ammonia separator (67) is connected to liquid ammonia tank; Exhaust outlet (6703) of the ammonia separator (67) is connected to unreacted gas pipeline (61) through the control valve (78); Unreacted gas pipeline (61) is connected to exhaust input interface (2305) of the plasma gasifier (23) through control valve (77), air pump (69) and the exhaust feedback pipeline (30); The leachate interfaces of the waste storage pit (2), the sorting machine (3) and spiral moisture expelling and feeding means (10) are connected to the material inlet of digester (9) through the ducts; Biogas outlet (902) of digester (9) is connected to biogas input interface (2308) of plasma gasifier (23) through biogas pipeline (11) and air pump (15);

Example 4

Figure 8:
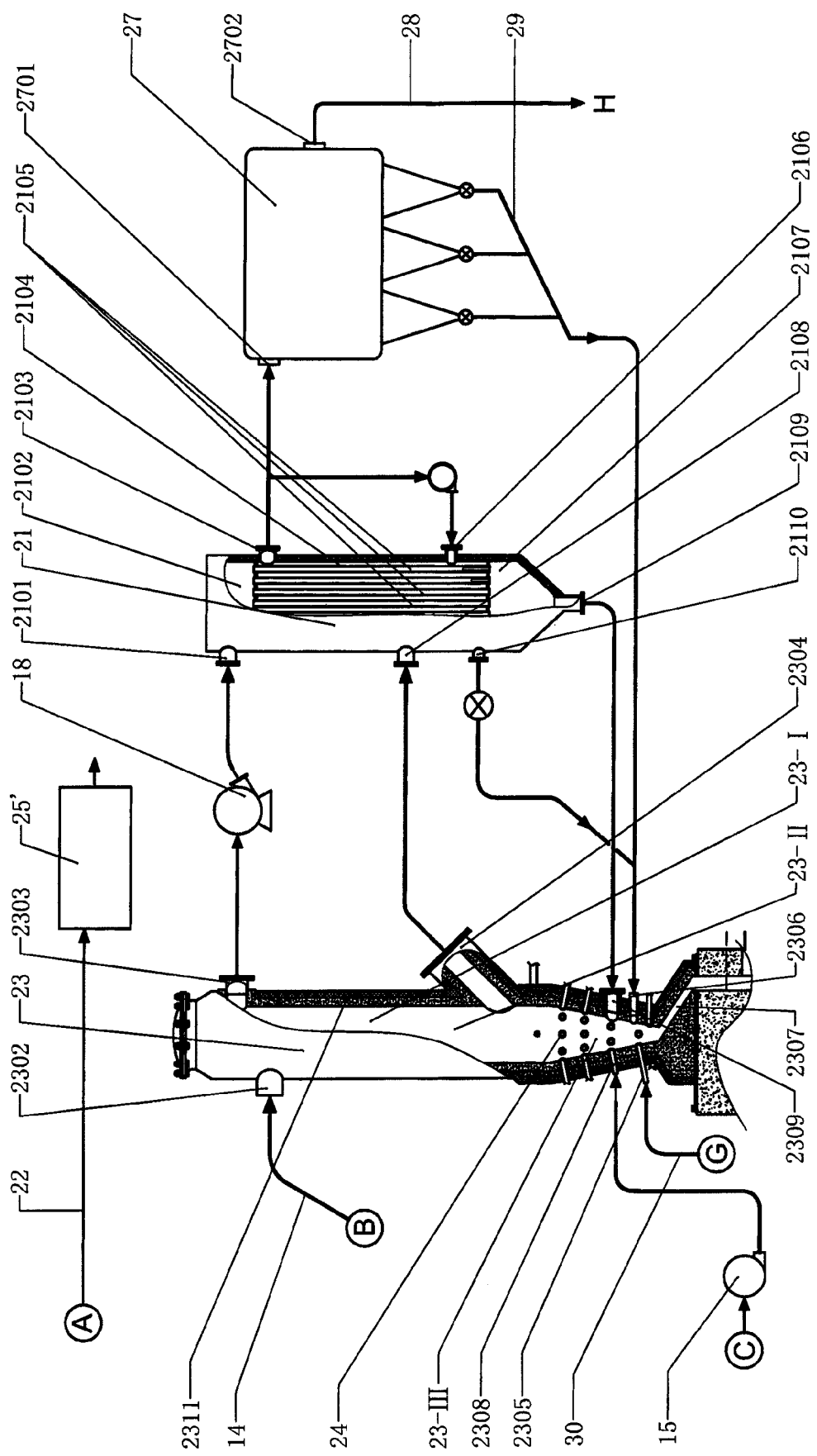
FIG. 8 is the detailed part of zone II-b in FIG. 3 and also a structural plan of gasification equipment in MSW disposal system.

As shown in the example of FIG. 8, a MSW gasification-liquefaction disposal system mainly comprises a plasma gasifier (23), a plasma torch (24), a circulating fan (18), a heat exchanger b (21) and connecting ducts. Among which: the plasma gasifier (23) takes high-furnace structure; Furnace wall (2311) of the plasma gasifier (23) consists of a fireproof layer, an insulating layer, a heat retaining layer and a steel shell in an order from interior to exterior; The fireproof layer is cast with high alumina refractory bricks or bauxite cement concrete. The insulating layer is made of diatomite material. The heat retaining layer is made of alumina silicate refractory fibrous material. The insulating layer in gasification section can be replaced by the cooling layer. The cooling layer consists of a steel pipe, a steel plate, an upper header pipe and a lower header pipe to constitute a water cooling wall structure. The lower header pipe is provided with an access of cooling water. The upper header pipe is provided with an outlet of backwater interface. The cooling layer is connected with a circulating cooling water system through the cooling water interface and backwater interface (not shown in figures). The plasma gasifier (23) is divided into a drying section (23-I), a pyrolysis section (23-II) and a gasification zone (23-III) from top to bottom. The drying section (23-I), pyrolysis section (23-II) and gasification zone (23-III) communicate directly. A waste material inlet (2302) and a pyrolysis gas outlet (2303) are provided in the upper part of drying section (23-I). Gasification section (-III) gasifier (23) is provided with input interface a (2309) of pyrolysis gas, the fly ash returning interface (2306) and connected with the biogas input interface (2308) and exhaust input interface (2305). A slag hole (2307) is provided in a side of lower part of the gasification section (23-III). A melted slag zone is provided between and taphole (2307). An output interface a (2304) of syngas is provided in the joint position of pyrolysis section (23-II) and gasification section (23-III). The furnace walls of drying section (23-I), pyrolysis section (23-II) and gasification section (23-III) are provided with a temperature sensor respectively. The furnace wall of gasification section (23-III) is also provided with a peepsight. The furnace wall of drying section (23-I) is also provided with a level sensor. The plasma torch (24) is provided in the furnace walls of gasification section (23-III) and melted slag zone. Multiple plasma torches are arranged ringwise in many layers. The plasma torch (24) is provided with working gas input interface, coolant output interface and power supply interface. Working gas input interface is connected to steam pipe work through control valve and connecting ducts. Coolant input & output interfaces are connected to the coolant supplying and returning interfaces of coolant equipment respectively. Power supply interface is connected to the power supply output end of plasma controller. The heat exchanger b (21) consists of an atmolysis chamber (2102), a heat exchange chamber (2104), a heat exchange bundle (2105) and a gas collection chamber (2107). The atmolysis chamber (2102), heat exchange chamber (2104) and gas collection chamber (2107) are arranged into upper, middle and lower parts. The atmolysis chamber (2102), heat exchange chamber (2104) and gas collection chamber (2107) are inside a steel shell. The exterior of the steel shell is covered with insulation material. Atmolysis chamber (2102) and heat exchange chamber (2104) are separated by a upper baffle. The heat exchange chamber (2104) and gas collection chamber (2107) are separated by a lower baffle. The heat exchange bundle (2105) is provided in the heat exchange chamber (2104), with both ends intersecting atmolysis chamber (2102) and gas collection chamber (2107). Atmolysis chamber (2102), heat exchange bundle (2105) and gas collection chamber (2107) constitute the returning passage of pyrolysis gas. The input interface b (2101) of pyrolysis gas is provided in atmolysis chamber (2102). Heat exchange chamber (2104)

is provided with syngas input interface (2108), syngas output interface b (2103), soot door (2106) and soot door (2110). The output interface (2109) of pyrolysis gas is provided in gas collection chamber (2107). The pyrolysis gas outlet (2303) in drying section of plasma gasifier (23) is connected to the air inlet of a circulating fan (18). The air outlet of the circulating fan (18) is connected to the input interface b (2101) of pyrolysis gas in atmolysis chamber. The output interface (2109) of pyrolysis gas in gas collection chamber of the heat exchanger b (21) is connected to input interface a (2309) of pyrolysis gas in the gasification section of plasma gasifier (23). The output interface a (2304) of syngas in plasma gasifier (23) is connected to the input interface (2108) of syngas in the heat exchange chamber of heat exchanger b (21). Syngas output interface b (2103) in the heat exchange chamber of the heat exchanger b (21) is connected into a downstream device. The soot door (2110) of the heat exchanger b (21) is connected to fly ash returning interface (2306) in the plasma gasifier (23). Soot-blowing opening (2106) of the heat exchanger b (21) is connected to an ash-blowing fan. The air inlet of ash-blowing fan is connected to syngas conveying pipeline and the air outlet of ash-blowing fan is connected to soot-blowing opening (2106) of the heat exchanger b (21).

Example 5

Figure 9:
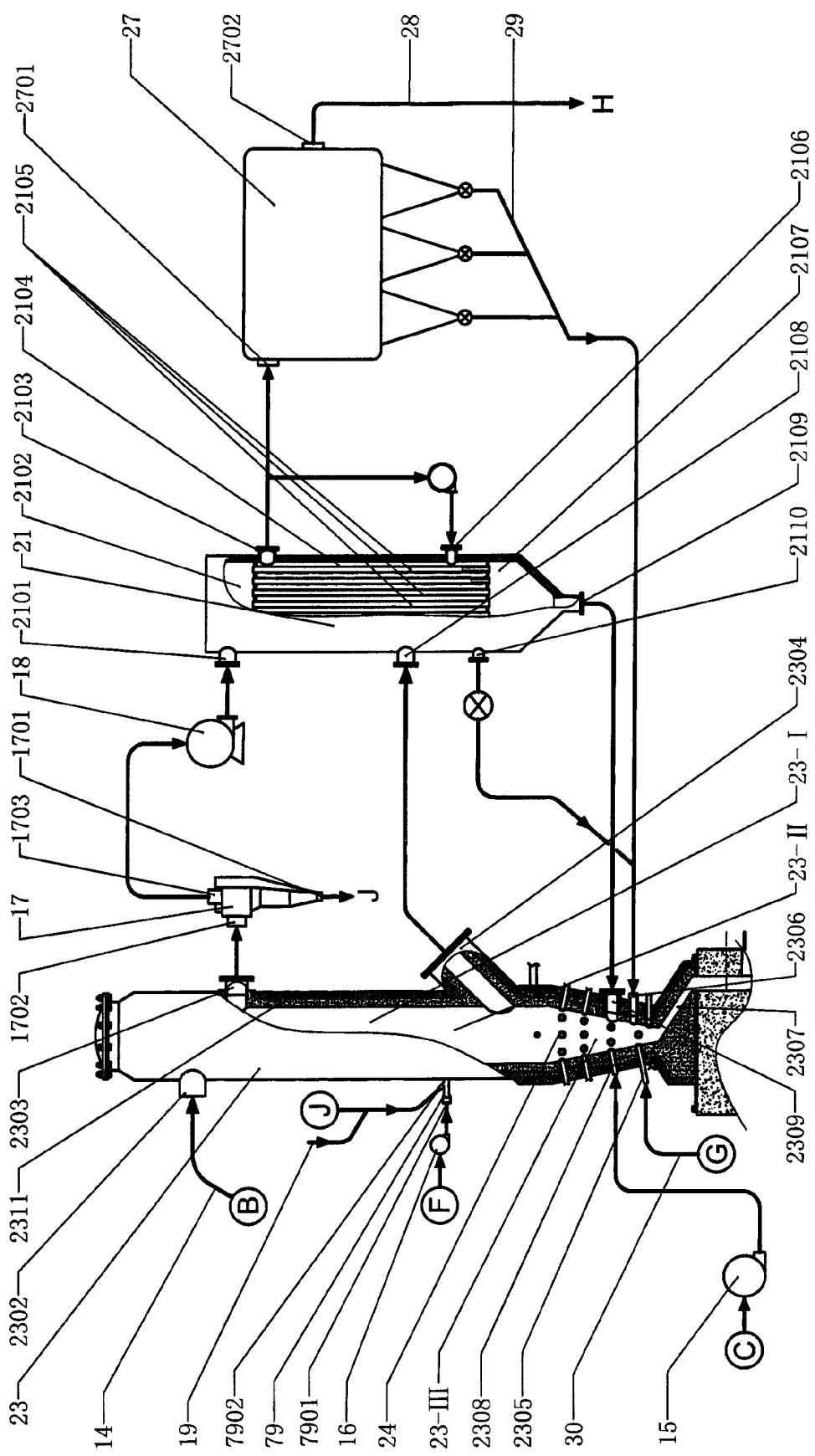
FIG. 9 is a structural plan of another gasification equipment in MSW disposal system.
Figure 10:
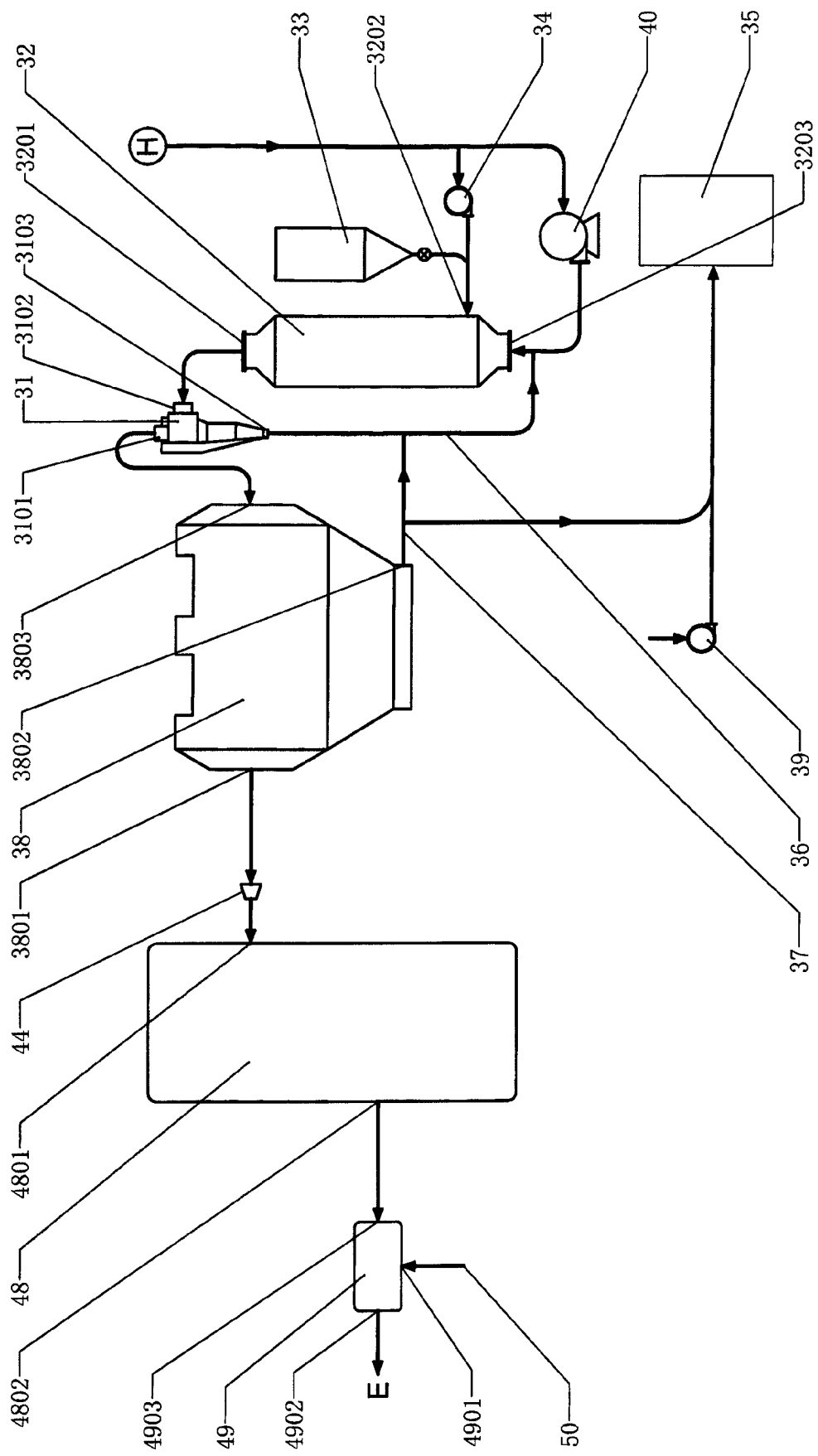
FIG. 10 is the detailed part of zone III-b in FIG. 3.

As shown in FIG. 9 of the present invention, this example has following changes on the basis of example 4: the furnace wall of pyrolysis section (23-II) of plasma gasifier (23) is provided with a calcium oxide torch (79); calcium oxide torch (79) is provided with $CO_2$ input interface (7901) and input interface of calcium oxide (7902); a gas-solid separator (17) is provided between pyrolysis gas outlet (2303) in the drying section of the plasma gasifier (23) and a circulating fan (18). The pyrolysis gas outlet (2303) in the drying section of the plasma gasifier (23) is connected to the mixture inlet (1702) of the gas-solid separator (17). The gaseous material outlet (1703) of the gas-solid separator (17) is connected to the air inlet of the circulating fan (18). The solid material outlet (1701) of the gas-solid separator (17) is connected to the input interface of calcium oxide (7902) of calcium oxide torch (79). Interface of calcium oxide supplementation (19) is provided in the connecting duct between the solid material outlet (1701) of amidships gas-solid separator (17) and input interface of calcium oxide (7902) of calcium oxide torch (79). $CO_2$ input interface (7901) of calcium oxide torch (79) is connected to the $CO_2$ gas pipeline through a material-blowing fan (16).

The invention claimed is:

1. A method for gasification-liquefaction disposal of municipal solid waste (MSW) using calcium oxide assisting plasma gasification technology, the method comprising the steps of:

dehydrating and sorting the MSW or an organic waste in a preprocessing process to reduce water and inorganic material contents, then feeding the dehydrated and sorted MSW or organic waste into a plasma gasifier through a $CO_2$ gas sealed feeding device;

providing the plasma gasifier with a drying section, a pyrolysis section and a gasification section in an order of upper, middle and lower segments;

drying, pyrolyzing and in the MSW or organic waste in the plasma gasifier to produce hydrogen-rich syngas in which CO and $H_2$ are main components;

providing a plasma torch in the gasification section of the plasma gasifier and using water steam as a gasifying agent and working gas;

heating the water steam by the plasma torch to >4200° C., so that water molecules are decomposed completely, generating H*, $H_2$*, HO*, O*, $O_2$* and $H_2O$* that are then directly sprayed on MSW carbon in the gasification section of the plasma gasifier, wherein MSW carbon serves as hydrogen and oxygen absorber to generate CO and $H_2$; adopting calcium oxide assisting plasma gasification, and providing a reaction chamber of a carbonator in the gasification system; the heat emitted by carbon dioxide absorbing calcium oxide to generate calcium carbonate can provide a supplementary heat source for the gasification, drying and preheating of new waste materials fed in the plasma gasifier, so as to reduce energy consumption of the plasma torch;

introducing the pyrolysis gas produced at the pyrolysis section of the plasma gasifier into the carbonator reaction chamber, and then as a carrier gas, the pyrolysis gas carrying calcium oxide, calcium carbonate mixture and heat into the drying section of the plasma gasifier; also serving as a dechlorination or desulfurizing agent, calcium oxide removing dioxin precursors, chlorides and sulfides in an environment of excessive calcium oxide; then introducing the pyrolysis gas into a gas-solid separator wherein calcium oxide and calcium carbonate are separated, and then fed into the gasification section of the plasma gasifier, so that methane, gaseous tar, ethylene, ethane, water steam, are pyrolyzed and chemically reacted to produce a 1 hydrogen-rich syngas wherein high-quality hydrogen and carbon monoxide are main components and dioxin is thoroughly decomposed at the same time;

outputting the hydrogen-rich syngas out of the plasma gasifier, and after cooling in an exhaust heat boiler, deacidifying and dedusting the hydrogen-rich syngas in a gas purifying equipment that consists of an absorption reactor, a cyclone duster and a bag dust collector;

absorbing carbon dioxide in the syngas by a potassium carbonate solution in a $CO_2$ absorbing tower to generate potassium bicarbonate;

feeding the syngas after removing carbon dioxide into a methanol synthesis reactor to produce methanol and feeding the potassium bicarbonate into a regeneration reactor to decompose to potassium carbonate solution and carbon dioxide by heating;

returning the decomposed potassium carbonate solution to the $CO_2$ absorbing tower for recycling and feeding the decomposed carbon dioxide into the carbonation reaction chamber of the gasification system for carbonation reaction with calcium oxide;

catalyzing the hydrogen-rich syngas to form methanol product in the methanol synthesis reactor;

mixing the methanol product with limewater in a mixing absorber of an end purifying device to allow residual contaminants and carbon dioxide to be absorbed by the limewater; then separating the methanol out through a distillation column, and returning unreacted gas to the methanol synthesis reactor for circulating reaction; after decontamination, feeding limewater back to the mixing absorber for recycling; and returning exhaust to the plasma gasifier for recycling, and forming a closed loop production system.

2. The method for gasification-liquefaction disposal of MSW according to claim 1, wherein operating temperature of the drying section is controlled at between 120 to 300° C.; operating temperature of the pyrolysis section is controlled between 300 to 1000° C.; operating temperature of the gasification section is controlled at between 1000 to 1300° C.;

operating pressure in the plasma gasifier is controlled at between −30 Pa~+5 kPa; when clinker is melted to a liquid slag and discharged, a liquid slag zone is provided between the gasification section and a slag port, and a plasma torch is provided in the slag zone; operating temperature of the slag zone is controlled at between 1300~1600° C.

3. A MSW gasification-liquefaction disposal system using a plasma gasification equipment, the system comprising a preprocessing device, a $CO_2$ gas sealed feeding device, a plasma gasifier, a plasma torch, a gas-solid separator, a circulating fan, a first heat exchanger, a carbonation reaction chamber, a waste heat boiler, an absorption reactor, a cyclone duster, a bag dust collector, a $CO_2$ absorber, a regeneration tower, a methanol synthesis reactor, a mixing absorber, a distillation column, a decontaminator, a circulating pump, a methanol tank and connecting ducts; wherein: the preprocessing device comprises a waste storage pit and a sorting machine; an inner space of plasma gasifier is provided with a drying section, a pyrolysis section and a gasification section; a waste material inlet, a heat carried gas inlet and a pyrolysis gas outlet are provided in the drying section; an output interface of heat carried gas is provided in the pyrolysis section; an input interface of pyrolysis gas is provided in the gasification section; an output interface of syngas is provided in a joint position of the pyrolysis section and the gasification section; the plasma torch is provided in the gasification section in a lower part of the plasma gasifier; a first heat exchanger consists of a atmolysis chamber, a heat exchange chamber and a gas collection chamber; an input interface of pyrolysis gas is provided in the atmolysis chamber; an output interface of heat carried gas is provided in the heat change chamber; an output interface of pyrolysis gas is provided in the gas collection chamber; the carbonation reaction chamber communicates directly with the heat exchange chamber in the first heat exchanger; the carbonation reaction chamber is provided with an input interface of heat carried gas, an inputting apparatus of the calcium oxide and an input interface of carbon dioxide; the $CO_2$ absorber is provided with an input interface of the syngas, an output interface of syngas, a $KHCO_3$ output interface and an input interface of the $K_2CO_3$ solution; the regeneration tower is provided with an input interface of $KHCO_3$, an output interface of $CO_2$ and an output interface of the $K_2CO_3$ solution;

the waste storage pit is constantly connected with the sorting machine through a crane grab; the sorting machine is constantly connected with a feed inlet of the $CO_2$ gas sealed feeding device of the plasma gasifier by a belt conveyor or screw feeders; an outlet of $CO_2$ gas sealed feeding device is connected to a waste inlet of the plasma gasifier; an output interface of heat carried gas of the plasma gasifier is connected to an input interface of heat carried gas of the carbonation reaction chamber; an output interface of heat carried gas of the first heat exchanger is connected to an inlet heat carried gas of the plasma gasifier; the outlet of heat carried gas of the plasma gasifier is connected to a mixture inlet of the gas-solid separator; a gaseous substance outlet of the gas-solid separator is connected to an input interface of pyrolysis gas of the first heat exchanger through a circulating fan; an output interface of pyrolysis gas of the first heat exchanger is connected to an input interface of pyrolysis gas of the plasma gasifier; an output interface of syngas of the plasma gasifier is connected to an input interface of syngas of the waste heat boiler; an output interface of syngas of the waste heat boiler is connected to an input interface of syngas of the absorption reactor; an output interface of syngas of the absorption reactor is connected to a mixture input interface of syngas of the cyclone duster; a solid substance outlet of the cyclone duster is connected to the connecting pipe of a syngas input interface of the absorption reactor; the solid gaseous substance outlet of the cyclone duster is connected to a syngas input interface of the bag dust collector; an output interface of syngas of the bag dust collector is connected to a syngas input interface of the $CO_2$ absorbing tower; an output interface of $KHCO_3$ of the $CO_2$ absorbing tower is connected to the input interface of $KHCO_3$ of the regeneration tower; the $CO_2$ output interface of the regeneration tower is connected to an input interface of $CO_2$ of the carbonation reaction chamber; the output interface of $K_2CO_3$ solution of the regenerating tower is connected to the input interface of $K_2CO_3$ solution of the $CO_2$ absorbing tower; the output interface of syngas of $CO_2$ absorbing tower is connected to an induction port of a first compressor; an exhaust port of the first compressor is connected to a virgin gas port of a methanol synthesis reactor; a methanol gas outlet of the methanol synthesis reactor is connected to a methanol gas inlet of the mixing absorber; a mixture outlet of mixing absorber is connected to a mixture input interface of the distillation column; an unreacted gas outlet of the distillation column is connected to a return-air interface of the methanol synthesis reactor via an unreacted gas pipeline and a second compressor; a methanol product outlet of the distillation column is connected to the methanol tank; a limewater outlet of the distillation column is connected to an input interface of the decontaminator; the limewater outlet of the decontaminator is connected to a water inlet of the circulating pump; a water outlet of the circulation pump is connected to a limewater inlet of the mixing absorber.

4. The system for gasification-liquefaction disposal of MSW according to claim 3, wherein the preprocessing device further comprises a spiral moisture expelling and feeding device and a digester; the spiral moisture expelling and feeding device is provided between the sorting machine and the $CO_2$ gas sealed feeding device; a waste material outlet of the sorting machine is constantly connected to a hopper of the spiral moisture expelling and feeding device through a belt conveyor; the material outlet of the spiral moisture expelling and feeding device is connected to a material inlet of $CO_2$ gas sealed feeding device through a first duct; the outlet of $CO_2$ gas sealed feeding device is connected to a material inlet of the plasma gasifier through a second duct; leachate interfaces of the waste storage pit, the sorting machine and the spiral moisture expelling and feeding device are connected to a material outlet of the digester; a biogas outlet of the digester is connected to the gasification section of the plasma gasifier.

5. The system for gasification-liquefaction disposal of MSW according to claim 3, wherein an induced-draft fan and a carbon monoxide conversion reactor are also provided between the bag dust collector and the $CO_2$ absorber; the output interface of syngas of bag dust collector is connected to a suction inlet of the induced-draft fan; an air outlet of the induced-draft fan is connected to a syngas input interface of the CO shift reactor; an output interface of syngas of the CO shift reactor is connected to the syngas input interface of $CO_2$ absorbing tower;

a third compressor and a syngas storage tank are also provided between the $CO_2$ absorbing tower and the first compressor; an output interface of syngas of the $CO_2$ absorbing tower is connected to an induction port of the third compressor; an exhaust port of the third compressor is connected to an input interface of the syngas storage tank; an output interface of the syngas storage tank is connected to a suction port of the first compressor;

an exhaust gas interface and a ammonia synthesizing equipment are provided in an unreacted gas pipeline at a terminal end of a methanol synthesis reactor, and meanwhile an exhaust feedback pipeline is provided between the plasma gasifier and a terminal end purification equipment; an exhaust gas interface of the unreacted gas pipeline is, via a control valve, respectively connected to the exhaust feedback pipeline of the plasma gasifier and a material inlet interface of the ammonia synthesizing equipment; an exhaust gas outlet of the ammonia synthesizing equipment is connected to the exhaust feedback pipeline of the plasma gasifier.

6. A MSW gasification-liquefaction disposal system using a plasma gasification equipment, the system comprising a preprocessing device, a $CO_2$ gas sealed feeding device, a plasma gasifier, a plasma torch, a circulating fan, a first heat exchanger, a waste heat boiler, an absorption reactor, a cyclone duster, a bag dust collector, a hydrogenation absorber, a methanol synthesis reactor, a mixing absorber, a distillation column, a decontaminator, a circulating pump, a methanol tank and connecting ducts; wherein: a preprocessing device comprises a waste storage pit and a sorting machine; an inner space of the plasma gasifier is provided with a drying section, a pyrolysis section and a gasification section; a waste material inlet and a pyrolysis gas outlet are provided in the drying section; an input interface of pyrolysis gas is provided in the gasification section; a syngas output interface is provided in a joint position of the pyrolysis section and the gasification section; the plasma torch is provided in gasification section in the lower part of the plasma gasifier; the second heat exchanger consists of an atmolysis chamber, a heat exchange chamber and a gas collection chamber; the input interface of pyrolysis gas is provided in the atmolysis chamber; the syngas input interface and output interface are provided in heat exchange chamber; an output interface of pyrolysis gas is provided in the gas collection chamber;

the waste storage pit is constantly connected with the sorting machine through a crane grab; the sorting machine is constantly connected with a feed inlet of the $CO_2$ gas sealed feeding device of the plasma gasification equipment by a belt conveyor or screw feeders; an outlet of $CO_2$ gas sealed feeding device is connected to an inlet of the plasma gasifier; a pyrolysis gas outlet of the plasma gasifier is connected to an input interface of pyrolysis gas of the second heat exchanger through the circulating fan; an output interface of pyrolysis gas of the second heat exchanger is connected to an input interface of pyrolysis gas in the gasification section of the plasma gasifier; an output interface of syngas of the plasma gasifier is connected to an input interface of syngas of the second heat exchanger; an output interface of syngas of the second heat exchanger is connected to an input interface of syngas of the waste heat boiler; an output interface of syngas of the waste heat boiler is connected to an input interface of syngas of the absorption reactor; an output interface of syngas of the absorption reactor is connected to a mixture input interface of syngas of the cyclone duster; a solid substance outlet of the cyclone duster is connected to a connecting pipe of the syngas input interface of the absorption reactor; a gaseous substance outlet of the cyclone duster is connected to a syngas input interface of the bag dust collector; an output interface of syngas of the bag dust collector is connected to an induction port of a first compressor; an exhaust port of the first compressor is connected to an input interface of a syngas storage tank; an output interface of the syngas storage tank is connected to an input interface of the hydrogenation mixer; an output interface of syngas of the hydrogenation mixer is connected to a suction inlet of a second compressor; an exhaust port of the second compressor is connected to a virgin gas port of the methanol synthesis reactor; a methanol gas outlet of the methanol synthesis reactor is connected to a methanol gas inlet of the mixing absorber; a mixture outlet of the mixing absorber is connected to a mixture input interface of a distillation column; an unreacted gas outlet of the distillation column is connected to a return-air interface of the methanol synthesis reactor via an unreacted gas pipeline and a third compressor; a methanol product outlet of the distillation column is connected to the methanol tank; a limewater outlet of the distillation column is connected to an input interface of the decontaminator; a limewater outlet of the decontaminator is connected to a water inlet of the circulating pump; a water outlet of the circulation pump is connected to a limewater inlet of the mixing absorber.

7. The system for gasification-liquefaction disposal of MSW according to claim 6, wherein the preprocessing device further comprises a spiral moisture expelling and feeding device and a digester; the spiral moisture expelling and feeding device is provided between the sorting machine and the $CO_2$ gas sealed feeding device; a waste material outlet of the sorting machine is constantly connected to a hopper of the spiral moisture expelling and feeding device through a belt conveyor; the material outlet of spiral moisture expelling and feeding device is connected to a material inlet of $CO_2$ gas sealed feeding device through a first duct; an outlet of $CO_2$ gas sealed feeding device is connected to the material inlet of the plasma gasifier through a second duct; leachate interfaces of the waste storage pit, the sorting machine and the spiral moisture expelling and feeding device are connected to a material outlet of the digester; a biogas outlet of the digester is connected to the gasification member of the plasma gasification furnace;

an induced-draft fan is also provided between the waste heat boiler and the absorption reactor; a syngas outlet of the waste heat boiler is connected to an air inlet of the induced-draft fan; an air outlet of the induced-draft fan is connected to the syngas input interface of the absorption reactor;

an exhaust gas interface and an ammonia synthesizing equipment are provided in an unreacted gas pipeline at a terminal end of a methanol synthesis reactor; meanwhile an exhaust feedback pipeline is provided between the plasma gasifier and the terminal end of the methanol synthesis reactor; an exhaust gas interface of the unreacted gas pipeline is, via a control valve, respectively connected to the exhaust feedback pipeline of the plasma gasifier and a material inlet interface of ammonia synthesizing equipment; the exhaust gas outlet of the ammonia synthesizing equipment is connected to the exhaust feedback pipeline of the plasma gasifier.

8. An equipment of gasification-liquefaction disposal for MSW, the equipment comprising a gasification device comprising a plasma gasifier, a plasma torch, a circulating fan, a first heat exchanger and connecting ducts; wherein: the plasma gasifier is divided into a drying section, a pyrolysis section and a gasification zone from top to bottom; the drying section, the pyrolysis section and the gasification zone communicate directly; the plasma torch is provided in a furnace wall of the gasification section; a waste material inlet and a pyrolysis gas outlet are provided in an upper part of the drying section; a first input interface of the pyrolysis gas is provided in the gasification section; a slag hole is provided in a lower part of the gasification section; a first output interface of syngas is provided in a joint position of the pyrolysis section and the gasification section; the first heat exchanger consists of an atmolysis chamber, a heat exchange chamber, a heat exchange bundle and a gas collection chamber; the atmolysis chamber, the heat exchange chamber and the gas collection chamber are arranged into upper, middle and lower parts, respectively; the heat exchange chamber is in the middle; the atmolysis chamber, the heat exchange chamber and the gas collection chamber are inside a steel shell; an exterior of the steel shell is covered with an insulation material; the atmolysis chamber and the heat exchange chamber are separated by an upper baffle; the heat exchange chamber and the gas collection chamber are separated by a lower baffle; the heat exchange bundle is provided in the heat exchange chamber, with both ends intersecting the atmolysis chamber and the gas collection chamber; the atmolysis chamber, the bundle and the gas collection chamber constitute a return passage of pyrolysis gas; a second input interface of pyrolysis gas is provided in the atmolysis chamber; the heat change chamber is provided with an input interface of syngas and a second output interface of syngas; an output interface of pyrolysis gas is provided in the gas collection chamber;

a pyrolysis gas outlet in the drying section of the plasma gasifier is connected to an air inlet of the circulating fan; an air outlet of the circulating fan is connected to the second input interface of pyrolysis gas in the atmolysis chamber of the first heat exchanger; the output interface of pyrolysis gas in the gas collection chamber of the first heat exchanger is connected to the first input interface of the pyrolysis gas in the gasification section of the plasma gasifier; the first output interface of syngas in the plasma gasifier is connected to an input interface of syngas in the heat exchange chamber of the first heat exchanger.

9. The equipment for gasification-liquefaction disposal of MSW according to claim 8, wherein a calcium oxide torch is provided in a furnace wall of the plasma gasifier; the calcium oxide torch is provided with a $CO_2$ input interface and a calcium oxide input interface; a gas-solid separator is provided between a pyrolysis gas outlets in a drying section of the plasma gasifier and an air inlet of the circulating fan; the pyrolysis gas outlet in the drying section of the plasma gasifier is connected to a mixture inlet of the gas-solid separator; a gaseous material outlet of the gas-solid separator is connected to the air inlet of the circulating fan; the solid material outlet of the gas-solid separator is connected to the input interface of the calcium oxide of the calcium oxide torch; the $CO_2$ input interface of the calcium oxide torch is connected to the $CO_2$ gas pipeline.

10. The equipment for gasification-liquefaction disposal of MSW according to claim 8, wherein the gasification section of the plasma gasifier is also provided with a fly ash returning interface, a biogas input interface and an exhaust gas input interface; a heat exchange chamber of the first heat exchanger is also provided with a soot-blowing opening and a soot door; the soot door of a first heat exchanger is connected to the fly ash returning interface in the plasma gasifier; the soot-blowing opening of the first heat exchanger is connected to a soot-blowing fan; the air inlet of the soot-blowing fan is connected to the syngas pipeline; the air outlet of the soot-blowing fan is connected to the soot-blowing opening of the first heat exchanger.

* * * * *